(12) United States Patent
Feldman et al.

(10) Patent No.: US 7,699,964 B2
(45) Date of Patent: Apr. 20, 2010

(54) MEMBRANE SUITABLE FOR USE IN AN ANALYTE SENSOR, ANALYTE SENSOR, AND ASSOCIATED METHOD

(75) Inventors: Benjamin Feldman, Oakland, CA (US); Zenghe Liu, Alameda, CA (US); Fei Mao, Fremont, CA (US); Adam Heller, Austin, TX (US)

(73) Assignee: Abbott Diabetes Care Inc., Alameda, CA (US)

( * ) Notice: Subject to any disclaimer, the term of this patent is extended or adjusted under 35 U.S.C. 154(b) by 1779 days.

(21) Appl. No.: 10/819,498

(22) Filed: Apr. 6, 2004

(65) Prior Publication Data

US 2005/0173245 A1 Aug. 11, 2005

Related U.S. Application Data

(63) Continuation-in-part of application No. 10/775,604, filed on Feb. 9, 2004, now abandoned.

(51) Int. Cl.
*G01N 27/40* (2006.01)
*G01N 27/327* (2006.01)
(52) U.S. Cl. .................. 204/296; 204/403.01; 600/345
(58) Field of Classification Search ............ 204/403.01, 204/295, 296; 600/345, 347
See application file for complete search history.

(56) References Cited

U.S. PATENT DOCUMENTS 3,164,534 A 1/1965 Free (Continued)

FOREIGN PATENT DOCUMENTS

DE 150656 9/1981

(Continued)

OTHER PUBLICATIONS

NiceZyme entry for EC 1.15.1.1, date unknown.*

(Continued)

*Primary Examiner*—Kaj K Olsen
(74) *Attorney, Agent, or Firm*—Edward J. Baba; Bozicevic, Field & Francis LLP

(57) ABSTRACT

A multifunctional membrane is provided. The multifunctional membrane is suitable for use in an analyte sensor. In a particular application, the multifunctional membrane may be used in connection with an amperometric biosensor, such as a transcutaneous amperometric biosensor. Some functions of the membrane are associated with properties of membrane itself, which is comprised of crosslinked polymers containing heterocyclic nitrogen groups. For example, the membrane, by virtue of its polymeric composition, may regulate the flux of an analyte to a sensor. Such regulation generally improves the kinetic performance of the sensor over a broad range of analyte concentration. Other functions of the membrane are associated with functional components, such as a superoxide-dismutating/catalase catalyst, either in the form of an enzyme or an enzyme mimic, that can be bound to the scaffold provided by the membrane. The effect of any such enzyme or enzyme mimic is to lower the concentration of a metabolite, such as superoxide and/or hydrogen peroxide, in the immediate vicinity of the sensing layer of the biosensor. Lowering the concentrations of such metabolites, which are generally deleterious to the function of the sensor, generally protects or enhances biosensor integrity and performance. The membrane is thus an important tool for use in connection with analyte sensors, amperometric sensors, biosensors, and particularly, transcutaneous biosensors. A membrane-covered sensor and a method for making same are also provided.

22 Claims, 7 Drawing Sheets

U.S. PATENT DOCUMENTS

| | | | |
|---|---|---|---|
| 4,550,076 A * | 10/1985 | Chikazawa et al. | 435/18 |
| 4,703,756 A | 11/1987 | Gough et al. | |
| 4,820,399 A | 4/1989 | Senda et al. | |
| 4,891,104 A | 1/1990 | Liston et al. | |
| 4,974,929 A | 12/1990 | Curry | |
| 5,200,051 A | 4/1993 | Cozzette et al. | |
| 5,202,317 A * | 4/1993 | Bruice | 514/185 |
| 5,217,966 A | 6/1993 | Bruice | |
| 5,227,405 A | 7/1993 | Fridovich et al. | |
| 5,262,035 A * | 11/1993 | Gregg et al. | 204/403.11 |
| 5,262,305 A | 11/1993 | Heller et al. | |
| 5,264,104 A | 11/1993 | Gregg et al. | |
| 5,320,725 A | 6/1994 | Gregg et al. | |
| 5,356,786 A | 10/1994 | Heller et al. | |
| 5,468,562 A | 11/1995 | Farivar et al. | |
| 5,593,852 A | 1/1997 | Heller et al. | |
| 5,610,293 A | 3/1997 | Riley et al. | |
| 5,640,954 A | 6/1997 | Pfeiffer et al. | |
| 5,651,869 A | 7/1997 | Yoshioka et al. | |
| 5,665,222 A | 9/1997 | Heller et al. | |
| 5,696,109 A | 12/1997 | Malfroy-Camine et al. | |
| 5,771,890 A | 6/1998 | Tamada | |
| 5,882,494 A | 3/1999 | Van Antwerp | |
| 5,906,921 A | 5/1999 | Ikeda et al. | |
| 5,914,026 A * | 6/1999 | Blubaugh et al. | 600/347 |
| 5,964,993 A | 10/1999 | Blubaugh, Jr. et al. | |
| 5,972,199 A | 10/1999 | Heller et al. | |
| 5,994,339 A | 11/1999 | Crapo et al. | |
| 6,011,077 A | 1/2000 | Müller | |
| 6,023,629 A | 2/2000 | Tamada | |
| 6,049,727 A | 4/2000 | Crothall | |
| 6,081,736 A | 6/2000 | Colvin et al. | |
| 6,084,093 A | 7/2000 | Riley et al. | |
| 6,091,976 A | 7/2000 | Pfeiffer et al. | |
| 6,103,033 A | 8/2000 | Say et al. | |
| 6,103,714 A | 8/2000 | Fridovich et al. | |
| 6,119,028 A | 9/2000 | Schulman et al. | |
| 6,120,676 A | 9/2000 | Heller et al. | |
| 6,122,536 A | 9/2000 | Sun et al. | |
| 6,127,356 A | 10/2000 | Crapo et al. | |
| 6,134,461 A | 10/2000 | Say et al. | |
| 6,143,164 A | 11/2000 | Heller et al. | |
| 6,144,869 A | 11/2000 | Berner et al. | |
| 6,175,752 B1 | 1/2001 | Say et al. | |
| 6,190,315 B1 | 2/2001 | Kost et al. | |
| 6,214,817 B1 | 4/2001 | Riley et al. | |
| 6,245,758 B1 | 6/2001 | Stern et al. | |
| 6,267,002 B1 | 7/2001 | Ehwald et al. | |
| 6,298,254 B2 | 10/2001 | Tamada | |
| 6,329,161 B1 | 12/2001 | Heller et al. | |
| 6,338,790 B1 | 1/2002 | Feldman et al. | |
| 6,368,274 B1 | 4/2002 | Van Antwerp et al. | |
| 6,372,045 B1 | 4/2002 | McCabe | |
| 6,400,974 B1 | 6/2002 | Lesho | |
| 6,403,788 B1 | 6/2002 | Meunier et al. | |
| 6,434,409 B1 | 8/2002 | Pfeiffer et al. | |
| 6,436,255 B2 | 8/2002 | Yamamoto et al. | |
| 6,438,414 B1 | 8/2002 | Conn et al. | |
| 6,448,239 B1 | 9/2002 | Groves et al. | |
| 6,466,810 B1 | 10/2002 | Ward et al. | |
| 6,475,181 B1 | 11/2002 | Potter et al. | |
| 6,477,395 B2 | 11/2002 | Schulman et al. | |
| 6,477,891 B2 | 11/2002 | Ehwald et al. | |
| 6,479,477 B1 | 11/2002 | Crapo et al. | |
| 6,491,657 B2 | 12/2002 | Rowe et al. | |
| 6,497,729 B1 | 12/2002 | Moussy et al. | |
| 6,508,785 B1 | 1/2003 | Eppstein | |
| 6,525,041 B1 | 2/2003 | Neumann et al. | |
| 6,530,915 B1 | 3/2003 | Eppstein et al. | |
| 6,541,490 B1 | 4/2003 | Campbell et al. | |
| 6,544,975 B1 | 4/2003 | Crapo et al. | |
| 6,560,471 B1 | 5/2003 | Heller et al. | |
| 6,573,257 B2 | 6/2003 | Malfroy-Camine et al. | |
| 6,589,948 B1 | 7/2003 | Malfroy-Camine et al. | |
| 6,591,126 B2 | 7/2003 | Roeper et al. | |
| 6,592,746 B1 | 7/2003 | Schmid-Schoenbein et al. | |
| 6,599,407 B2 | 7/2003 | Taniike et al. | |
| 6,602,678 B2 | 8/2003 | Kwon et al. | |
| 6,620,123 B1 | 9/2003 | Mitragotri et al. | |
| 6,679,841 B2 | 1/2004 | Bojan et al. | |
| 6,685,699 B1 | 2/2004 | Eppstein et al. | |
| 6,702,857 B2 | 3/2004 | Brauker et al. | |
| 6,740,215 B1 | 5/2004 | Nakaminami et al. | |
| 6,741,877 B1 | 5/2004 | Shults et al. | |
| 6,746,582 B2 | 6/2004 | Heller et al. | |
| 6,770,729 B2 | 8/2004 | Van Antwerp | |
| 6,885,196 B2 | 4/2005 | Taniike et al. | |
| 2001/0039393 A1 | 11/2001 | Mori et al. | |
| 2001/0041830 A1 | 11/2001 | Varalli et al. | |
| 2002/0006634 A1 | 1/2002 | Han et al. | |
| 2002/0042407 A1 | 4/2002 | Fridovich et al. | |
| 2002/0082490 A1 | 6/2002 | Roeper et al. | |
| 2003/0031699 A1 | 2/2003 | Van Antwerp | |
| 2003/0042137 A1 * | 3/2003 | Mao et al. | 204/403.01 |
| 2003/0055032 A1 | 3/2003 | Groves et al. | |
| 2003/0065254 A1 | 4/2003 | Schulman et al. | |
| 2003/0069281 A1 | 4/2003 | Fridovich et al. | |
| 2003/0077702 A1 | 4/2003 | Shah et al. | |
| 2003/0077772 A1 | 4/2003 | Shah et al. | |
| 2003/0078560 A1 | 4/2003 | Miller et al. | |
| 2003/0099682 A1 | 5/2003 | Moussy et al. | |
| 2003/0118577 A1 | 6/2003 | Weill et al. | |
| 2003/0199837 A1 | 10/2003 | Vachon | |
| 2003/0217966 A1 | 11/2003 | Tapsak et al. | |
| 2004/0028612 A1 | 2/2004 | Singaram et al. | |
| 2004/0064133 A1 | 4/2004 | Miller et al. | |
| 2004/0074785 A1 | 4/2004 | Holker et al. | |
| 2005/0031689 A1 | 2/2005 | Shults et al. | |
| 2005/0033132 A1 | 2/2005 | Shults et al. | |

FOREIGN PATENT DOCUMENTS

| | | |
|---|---|---|
| EP | 1 153 571 A1 | 11/2001 |
| WO | WO 94/10560 A1 | 5/1994 |
| WO | WO 95/31197 A1 | 11/1995 |
| WO | WO 98/17199 A2 | 4/1998 |
| WO | WO 98/43637 A1 | 10/1998 |
| WO | WO 99/47471 A1 | 9/1999 |
| WO | WO 00/75144 A1 | 12/2000 |
| WO | WO 00/78293 A1 | 12/2000 |
| WO | WO 01/36660 A2 | 5/2001 |
| WO | WO 02/44187 * | 6/2002 |
| WO | WO 03/063925 A1 | 8/2003 |
| WO | WO 03/076893 A2 | 9/2003 |
| WO | WO 2004/028337 A2 | 4/2004 |

OTHER PUBLICATIONS

Batinić-Haberle, "Manganese Porphyrins and Related Compounds as Mimics of Superoxide Dismutase," *Methods Enzymol*, 349, 2002, pp. 223-233.

Chan et al., "Free Fatty Acids, Oxygen Free Radicals, and Membrane Alterations in Brain Ischemia and Injury," *Cerebrovascular Diseases*, 1985, pp. 161-171.

Chan et al., "Protective Effects of Liposome-Entrapped Superoxide Dismutase on Posttraumatic Brain Edema," *Annals of Neurology*, vol. 21, No. 6, Jun. 1987, pp. 540-547.

Csöregi et al., "Design, Chracterization, and One-Point in Vivo Calibration of a Subcutaneously Implanted Glucose Electrode," *Analytical Chemistry*, vol. 66, No. 19, Oct. 1, 1994, pp. 3131-3138.

Csöregi et al., "Design and Optimization of a Selective Subcutaneously Implantable Glucose Electrode Based on 'Wired' Glucose Oxidase," *Analytical Chemistry*, vol. 67, No. 7, Apr. 1, 1995, pp. 1240-1244.

Doctrow et al., "Salen-Manganese Complexes: Combined Superoxide Dismutase/Catalase Mimics with Broad Pharmacological Efficacy," *Advances in Pharmacology*, vol. 38, 1997, pp. 247-269.

McGowan et al., "Spurious Reporting of Nocturnal Hypoglycemia by CGMC in Patients with Tightly Controlled Type 1 Diabetes," *Diabetes Care*, vol. 25, No. 9, Sep. 2002, pp. 1499-1503.

Mabley et al., "Part II: Beneficial Effects of the Peroxynitrite Decomposition Catalyst FP15 in Murine Models of Arthritis and Colitis," *Molecular Medicine*, vol. 8, No. 10, Oct. 2002, pp. 581-590.

Metzger et al., "Reproducibility of Glucose Measurements Using the Glucose Sensor," *Diabetes Care*, vol. 25, No. 6, Jul. 2002, pp. 1185-1191.

Pacher et al., "Potent Metalloporphyrin Peroxynitrite Decomposition Catalyst Protects Against the Development of Doxorubicin-Induced Cardiac Dysfunction," *Circulation*, Feb. 18, 2003, vol. 107, No. 6. pp. 896-904.

Riley, "Functional Mimics of Superoxide Dismutase Enzymes as Therapeutic Agents," *Chemical Reviews*, 1999, vol. 99, No. 9, pp. 2573-2587.

Salvemini et al., "Superoxide Dismutase Mimetics," *Pulmonary Pharmacology & Therapeutics*, 2002, vol. 15, pp. 439-447.

Schmidtke et al., "Measurement and Modeling of the Transient Difference Between Blood and Subcutaneous Glucose Concentrations in the Rate after Injection of Insulin," *Proc. Natl. Acad. Sci. USA*, vol. 95. 1998. pp. 294-299.

Schmidtke et al., "Accuracy of the One-Point in Vivo Calibration of 'Wired' Glucose Oxidase Electrodes Implanted in Jugular Veins of Rates in Periods of Rapid Rise and Decline of the Glucose Concentration," *Analytical Chemistry*. vol. 70. No. 10. May 15, 1998. pp. 2149-2155.

Schmidtke et al., "Statistics for Critical Clinical Decision Making Based on Readings of Pairs of Implanted Sensors," *Analytical Chemistry*, vol. 68, No. 17, Sep. 1, 1996, pp. 2845-2849.

Szabó et al., Part I: Pathogenetic Role of Peroxynitrite in the Development of Diabetes and Diabetic Vascular Complications: Studies with FP15, A Novel Potent Peroxynitrite Decomposition Catalyst, *Molecular Medicine*. vol. 8. No. 10. Oct. 2002. pp. 571-579.

Thomé-Duret et al., "Use of a Subcutaneous Glucose Sensor to Detect Decreases in Glucose Concentration Prior to Observation in Blood," *Analytical Chemistry*, vol. 68, No. 21, Nov. 1, 1996, pp. 3822-3826.

Udipi et al., "Modification of Inflammatory Response to Implanted Biomedical Materials in vivo by Surface Bound Superoxide Dismutase Mimics," *J. Biomed. Mater. Res.* 2000, vol. 51, No. 4, pp. 549-560.

Weiss et al., "Manganese-Based Superoxide Dismutase Mimetics Inhibit Neutrophil Infiltration in vivo," *The Journal of Biological Chemistry*, vol. 271, No. 42, Oct. 18, 1996, pp. 26149-26156.

Notification of Transmittal of the International Search Report and the Written Opinion of the International Searching Authority, or the Declaration, International Application No. PCT/US2005/002821 for TheraSense, Inc., mailed Jun. 9, 2005.

DirecNet Study Group, "Accuracy of the GlucoWatch G2 Biographer and the Continuous Glucose Monitoring System During Hypoglycemia," *Diabetes Care*, vol. 27, No. 3, Mar. 2004, pp. 722-726.

Tamada et al., The Effect of Preapplication of Corticosteroids on Skin Irritation and Performance of the GlucoWatch G2® Biographer, *Diabetes Technology & Therapeutics*, vol. 6, No. 3, 2004, pp. 357-367.

Monsod et al., "Do Sensor Glucose Levels Accurately Predict Plasma Glucose Concentrations During Hypoglycemia and Hyperinsulinemia?" *Diabetes Care*, vol. 25, No. 5, May 2002, pp. 889-893.

Mauras, M.D., et al., "Lack of Accuracy of Continuous Glucose Sensors in Healthy, Nondiabetic Children: Results of the Diabetes Research in Children Network (DirecNet) Accuracy Study," *The Journal of Pediatrics*, Jun. 2004, pp. 770-775.

Kaufman, M.D., et al., "Nocturnal Hypoglycemia Detected with the Continuous Glucose Monitoring System in Pediatric Patients with Type 1 Diabetes," *Journal of Pediatrics*, Nov. 2002, pp. 625-630.

Feldman, Ph.D., et al., "A Continuous Glucose Sensor Based on Wired Enzyme™ Technology—Results from a 3-Day Trial in Patients with Type 1 Diabetes," *Diabetes Technology & Therapeutics*, vol. 5, No. 5, 2003, pp. 769-779.

Gamache et al., "Simultaneous Measurement of Monoamines, Metabolites and Amino Acids in Brain Tissue and Microdialysis Perfusates," *Journal of Chromatography*, 614 (1993) pp. 213-220.

Niwa et al., "Concentration of Extracellullar L-Glutamate Released from Cultured Nerve Cells Measured with a Small-Volume Online Sensor," *Anal.Chem.*, 1996, 68, pp. 1865-1870.

Heller et al., "Amperometric Biosensors Based on Three-Dimensional Hydrogel-Forming Epoxy Networks," *Sensor and Actutators B*, 13-14, 1993, pp. 180-183.

Maidan et al., "Elimination of Electrooxidizable Interferants in Glucos Electrodes," *J. Am. Chem. Soc.* 1991, 113, pp. 9003-9004.

Maidan et al., "Elimintation of Electrooxidizable Interferant-Produced Currents in Amperometric Biosensors," *Anal. Chem.*, 1992, 64, pp. 2889-2896.

* cited by examiner

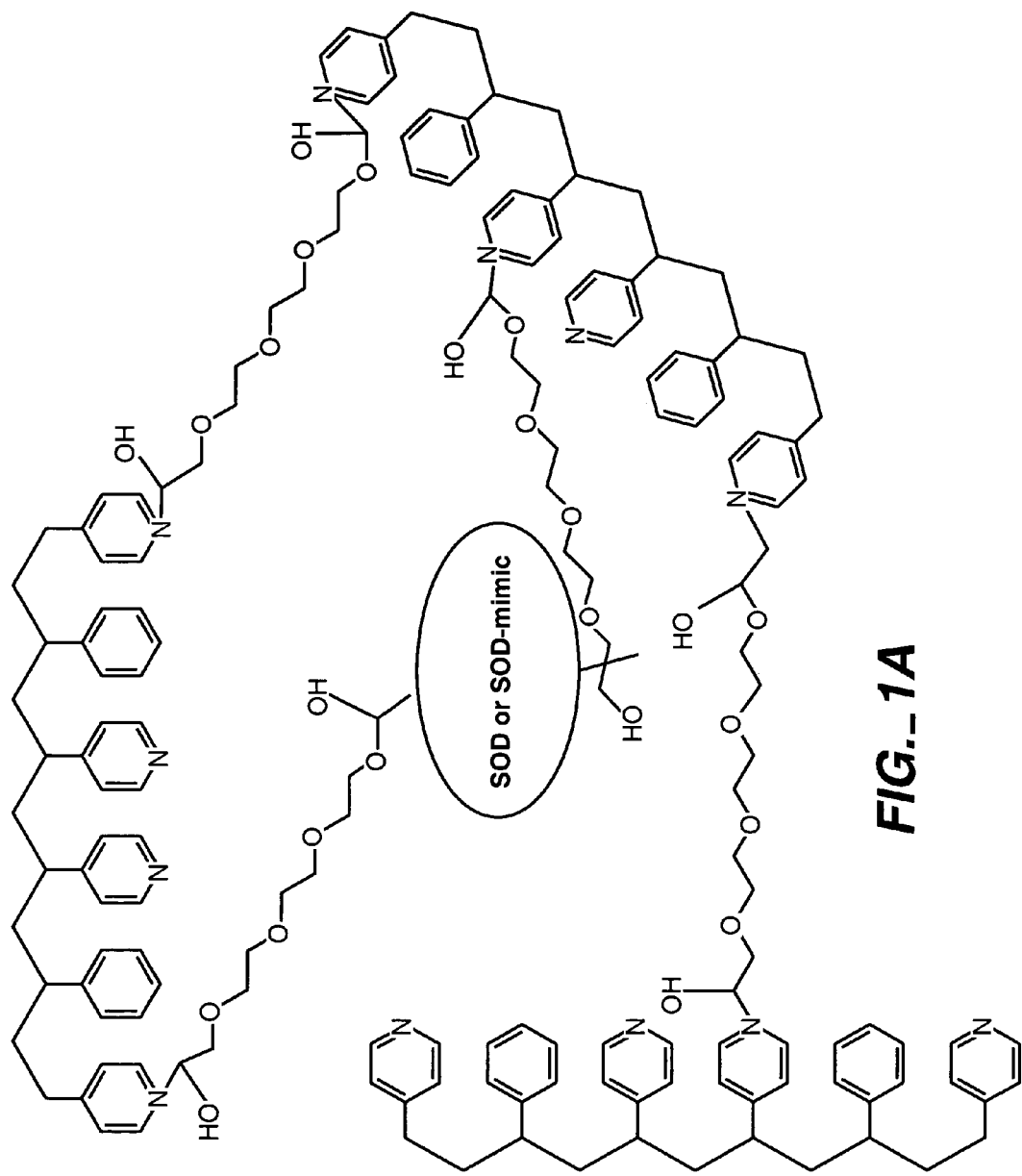
FIG._1A

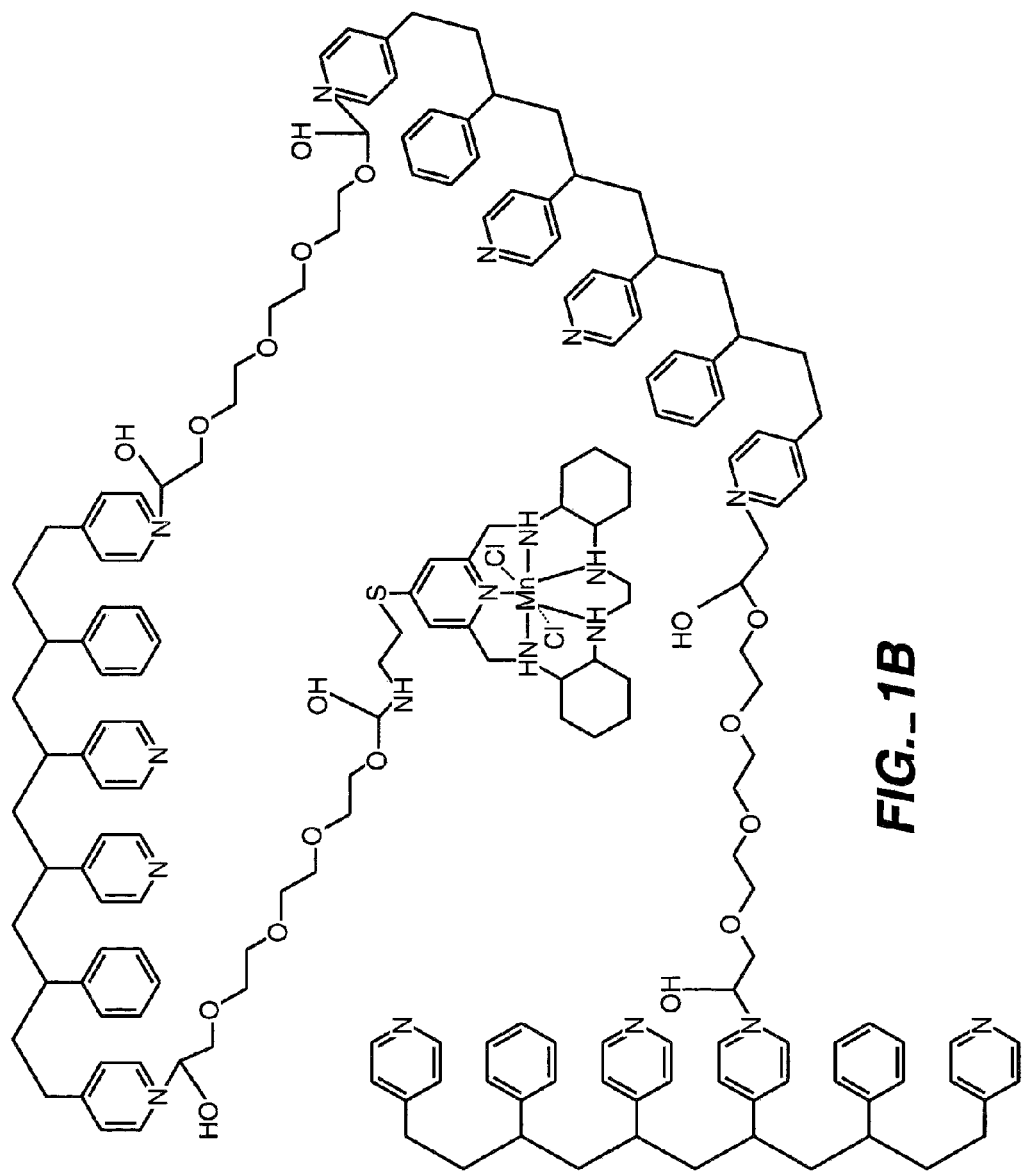
FIG._1B

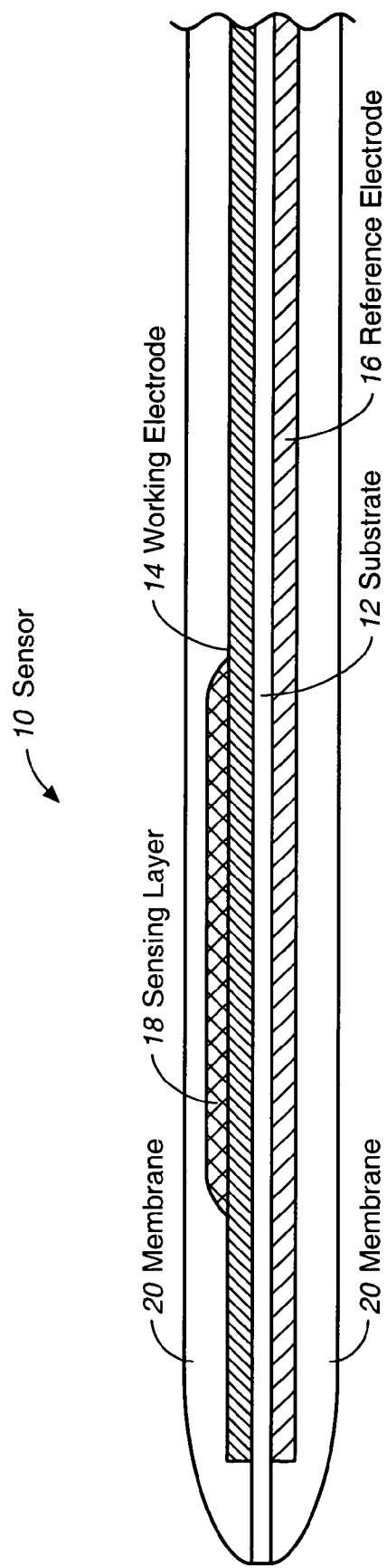
FIG._2A

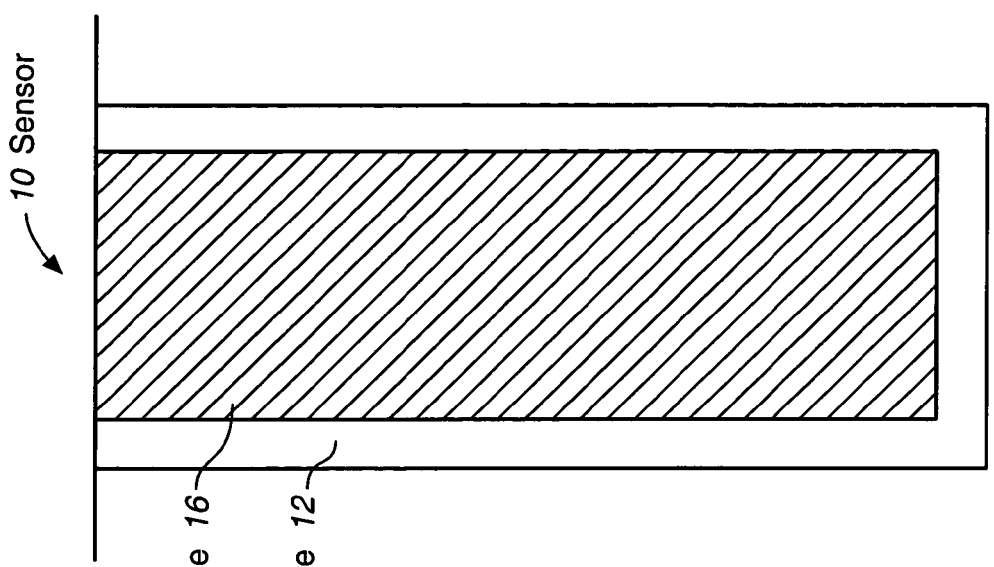
*FIG._2C*
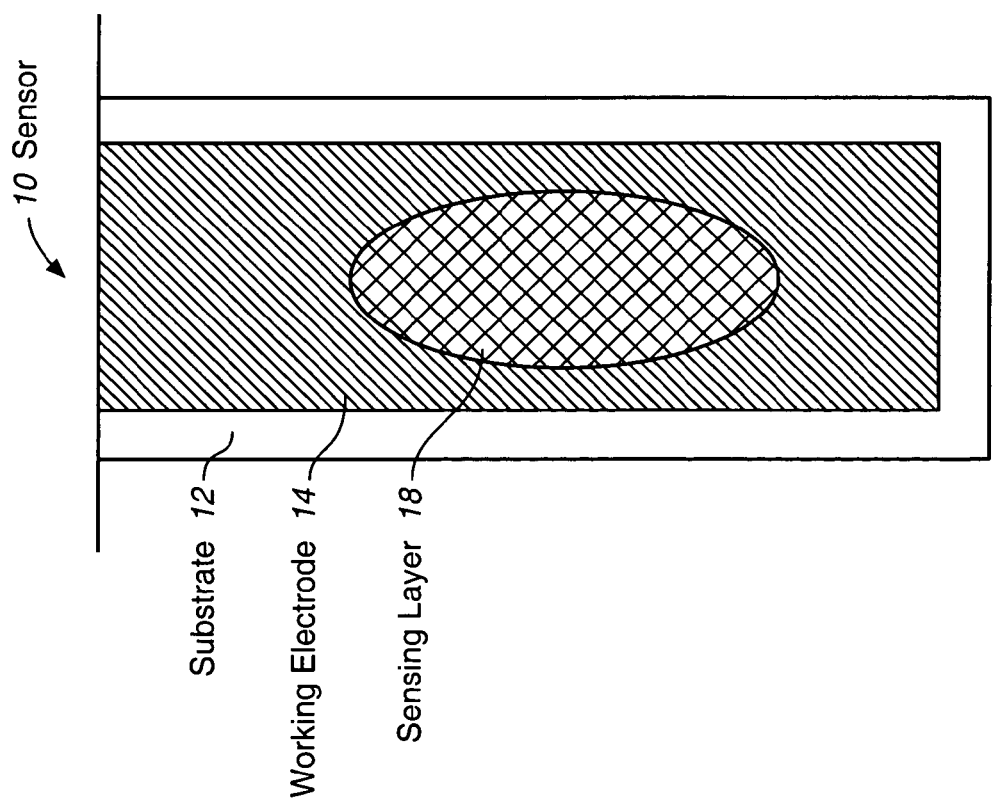
*FIG._2B*

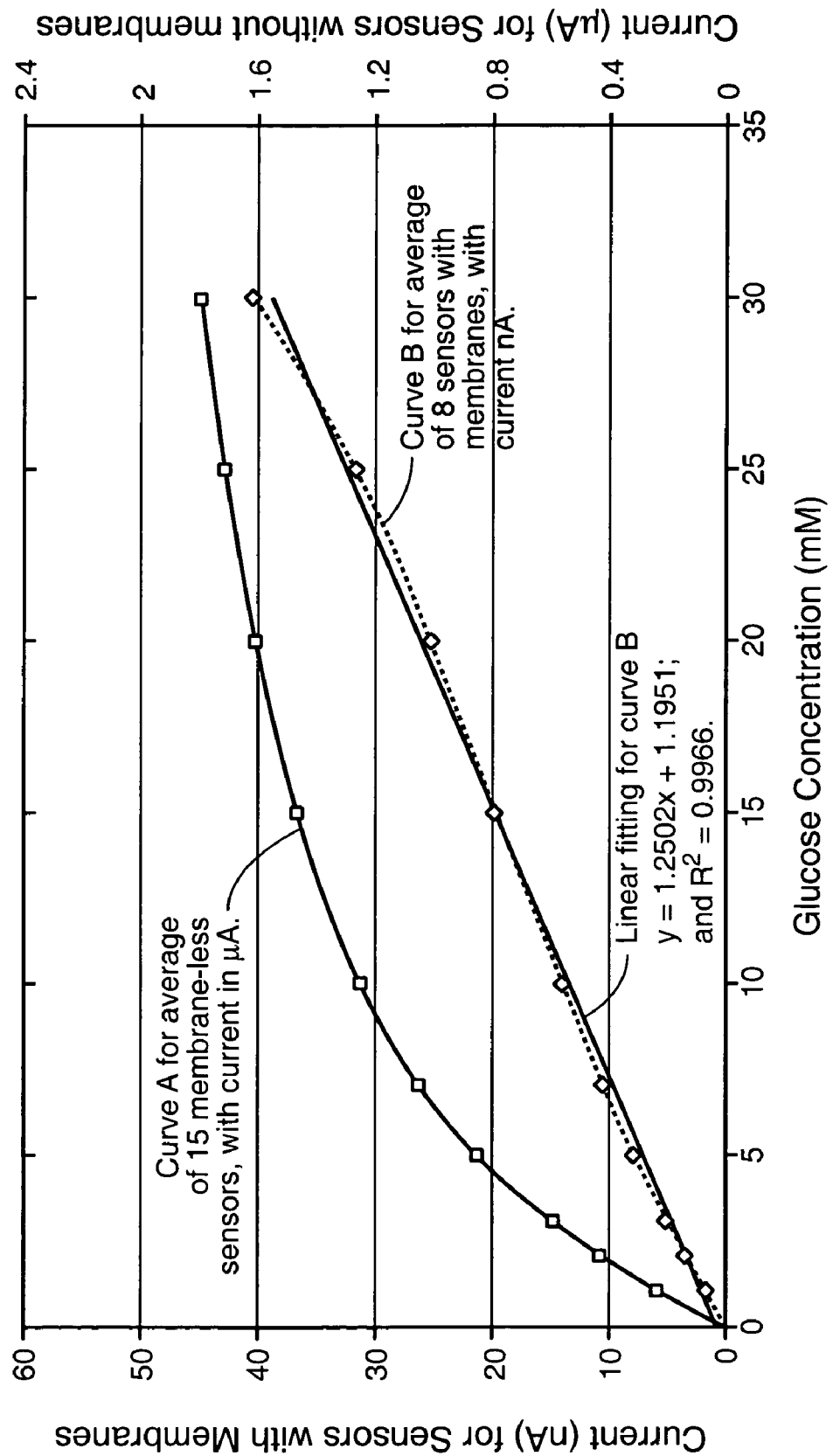
FIG._3

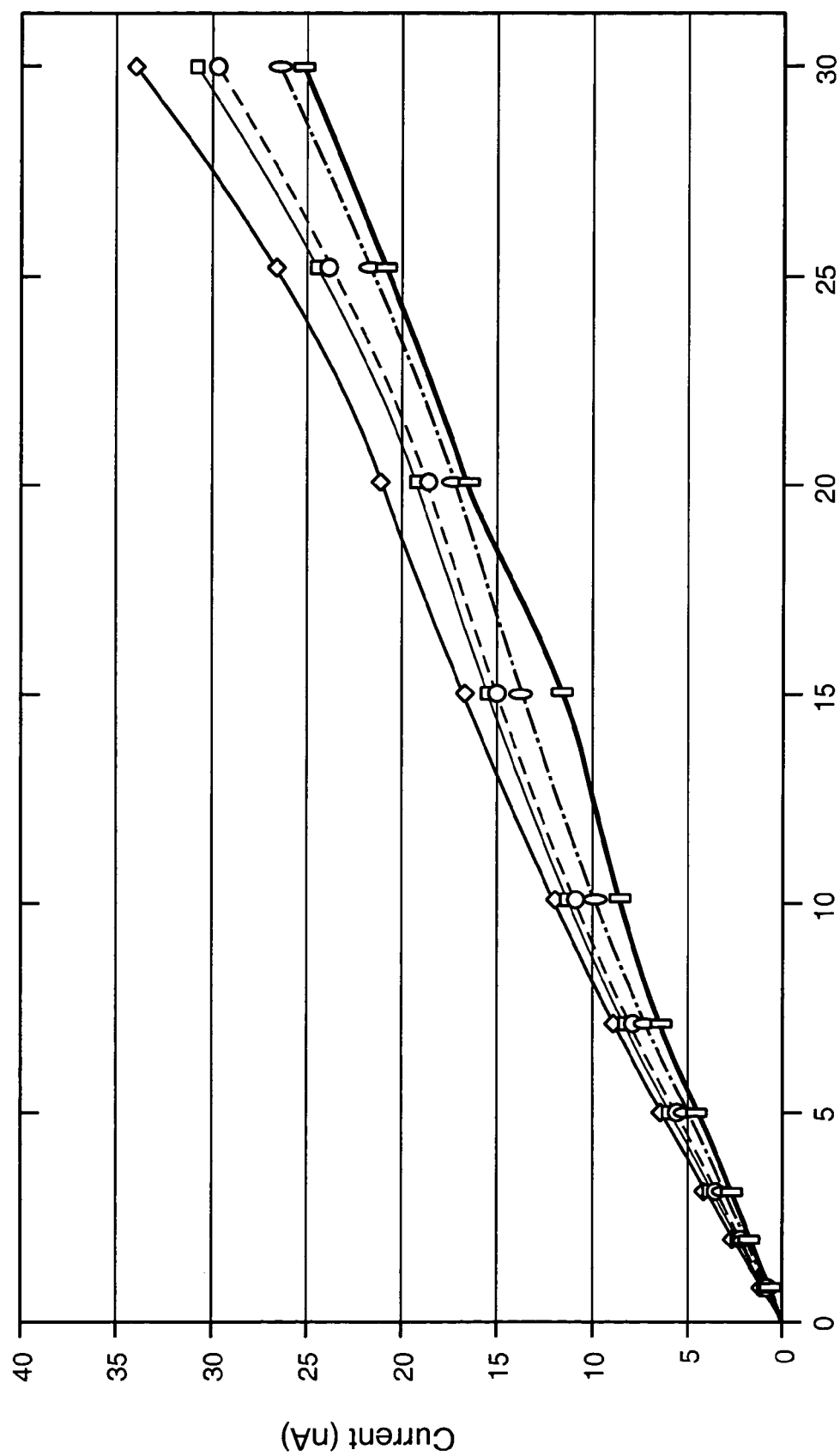
FIG._4

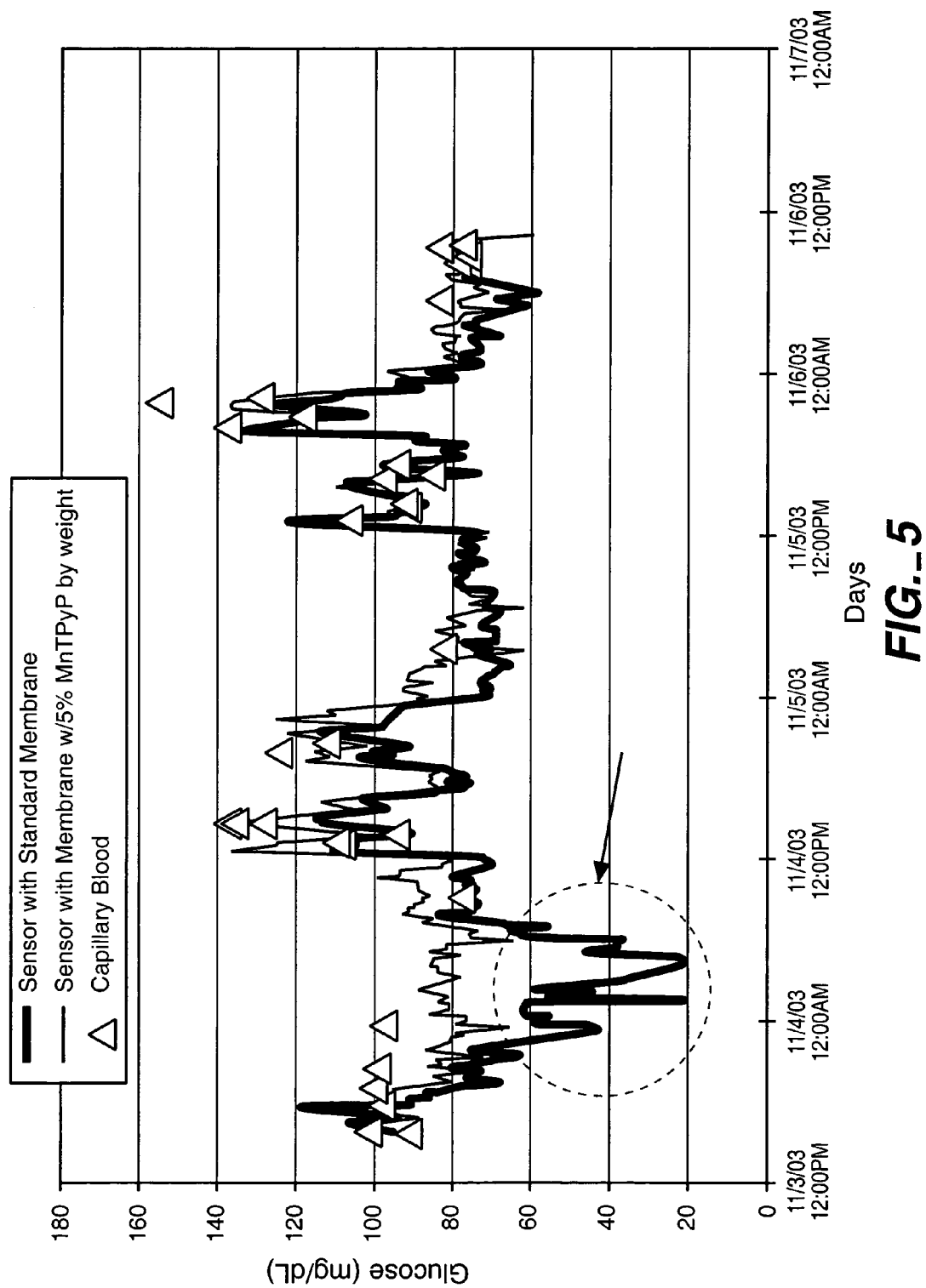
FIG._5

MEMBRANE SUITABLE FOR USE IN AN ANALYTE SENSOR, ANALYTE SENSOR, AND ASSOCIATED METHOD

CROSS-REFERENCE TO RELATED APPLICATIONS

This application is related to U.S. patent application Ser. No. 10/775,604 of Feldman et al., which was filed on Feb. 9, 2004, as a continuation-in-part thereof, now abandoned and is additionally related to U.S. patent application Ser. No. 10/146,518 of Mao et al., which was filed on May 14, 2002, the corresponding U.S. Patent Application Publication No. U.S. 2003/0042137 A1 of Mao et al., which was published on Mar. 6, 2003, now U.S. Pat. No. 6,932,894 and U.S. Provisional Patent Application No. 60/291,215 of Mao, which was filed on May 15, 2001. Each of the aforementioned applications, publication, and provisional application, is incorporated in its entirety herein by this reference.

FIELD OF THE INVENTION

This invention generally relates to a membrane with multiple functions, such as providing a protective layer, regulating flux of an analyte, and/or providing catalytic activity. The invention relates to such a multifunctional membrane that may be used in connection with an analyte sensor, such as a biosensor that operates while placed transcutaneously with respect to a living body.

BACKGROUND OF THE INVENTION

Enzyme-based biosensors are devices in which a signal from an analyte-concentration-dependent biochemical reaction is converted into a measurable optical or electrical signal. Amperometric, enzyme-based biosensors typically employ two or three electrodes, including at least one measuring or working electrode and one reference electrode. The working electrode is composed of a non-corroding carbon or a metal conductor and is connected to the reference electrode via a circuit, such as a potentiostat. The working electrode typically includes a sensing layer in direct contact with the conductive material of the electrode. The sensing layer may include an enzyme, an enzyme stabilizer such as bovine serum albumin (BSA), and a crosslinker that crosslinks the sensing layer components. Alternatively, the sensing layer may include an enzyme, a polymeric mediator, and a crosslinker that crosslinks the sensing layer components, as in a "wired-enzyme" biosensor.

In an example of an amperometric, enzyme-based, glucose biosensor, the sensor utilizes glucose oxidase, which catalyzes the oxidation of glucose by oxygen in a sample of body fluid and generates gluconolactone and hydrogen peroxide, whereupon the hydrogen peroxide is electrooxidized and correlated to the concentration of glucose in the sample (Thom-Duret et al., Anal. Chem. 68, 3822 (1996); and U.S. Pat. No. 5,882,494 of Van Antwerp et al., filed on Aug. 28, 1995). In another example of an amperometric, enzyme-based, glucose biosensor, a polymeric redox mediator "wires" the reaction center of glucose oxidase to an electrode and catalyzes the electrooxidation of glucose to gluconolactone. The principle and the operational details of such a "wired-enzyme" biosensor have been described (Csoregi, et al., Anal. Chem. 1994, 66, 3131; Csoregi, et al., Anal. Chem. 1995, 67, 1240; Schmidtke, et al., Anal. Chem. 1996, 68, 2845; Schmidtke, et al., Anal. Chem. 1998, 70, 2149; and Schmidtke, et al., Proc. Natl. Acad. Sci. U.S.A. 1998, 95, 294).

The operation and performance of an amperometric biosensor, such as those just described, may be complicated at high rates of analyte flux. For example, at high rates of glucose flux, an amperometric glucose biosensor may be kinetically overwhelmed, such that the relationship between the concentration of glucose in a sample fluid and the response from the biosensor becomes non-linear. This kinetic problem may be solved by the interposition of an analyte-flux-limiting membrane between the sample fluid and the sensing layer of the biosensor, as described in the above-mentioned U.S. Patent Application Publication No. U.S. 2003/0042137 A1 of Mao et al. Still, the development of analyte-flux-limiting membranes, such as glucose-flux-limiting membranes, has not been without its challenges. Many known membranes have proved difficult to manufacture and/or have exhibited properties that limit their practical use, such as practical use in a living body.

Various biosensors have been designed to operate partially or wholly in a living body. Indeed, clinical use of such biosensors has been a significant step toward helping diabetic patients achieve tight control over their blood glucose levels. However, some of these biosensors have been known to provide spurious, low-glucose-reading incidents, particularly during periods of stillness, such as when a subject is asleep. For example, Metzger et al. and McGowan et al. have demonstrated that the CGMS continuous glucose monitoring system of Medtronic MiniMed (Northridge, Calif.) provides such spurious, low-glucose-reading incidents. (See Metzger et al., Reproducibility of glucose measurements using the glucose sensor, Diabetes Care, July 2002, Vol. 25, 1185-1191; and McGowan et al., Spurious reporting of nocturnal hypoglycemia by CGMS in patients with tightly controlled type 1 diabetes, Diabetes Care, September 2002, Vol. 25, 1499-1503.) These low-glucose-reading incidents are very problematic, particularly in the monitoring and treatment of a diabetic subject, as they indicate that a subject is hypoglycemic when the subject is not. As an example, when a spurious, low glucose reading is used as a signal to control insulin dosage, a subject may receive an improper or a reduced dose of insulin and thus be put at risk or in actual danger.

The cause of low-glucose-reading incidents has not been understood and no specific hypotheses as to the cause of these incidents have been put forward for consideration, testing, analysis, or evaluation. For example, while Metzger et al. and McGowan et al. noted that the above-mentioned CGMS system of Medtronic MiniMed measures interstitial fluid glucose levels, rather than capillary glucose levels, and that there may be a slight time lag between the two if the blood glucose level is changing rapidly, this does not adequately explain the occurrence of low-glucose-reading incidents. (Id.) Further, neither Metzger et al. nor McGowan et al. provided a hypothesis as to the cause of these low-glucose-reading incidents.

Further development of biosensor components and biosensors is desirable.

SUMMARY OF THE INVENTION

The present invention is directed to multifunctional membranes and sensors, such as transcutaneous electrochemical biosensors, equipped with such membranes. By way of example, a sensor or biosensor, such as any of the transcutaneous electrochemical sensors described in U.S. Pat. No. 6,560,471 of Heller et al., filed on Jan. 2, 2001, may be equipped with a multifunctional membrane, according to the present invention. The membranes, composed of crosslinked polymers containing heterocyclic nitrogen groups, are covalently or otherwise associated with various enzymes and/ or enzyme mimics. The polymeric membranes, such as those composed of polyvinylpyridine and/or polyvinylimidazole polymers, for example, function to regulate the flux of an analyte, such as glucose, to a working electrode in an electrochemical sensor. As such, the polymeric membranes may facilitate the linear responsiveness, calibration, and/or stability of the sensor. Additionally, the membranes, with which enzymes and/or enzyme mimics are associated, function to regulate the concentration of superoxide and/or hydrogen peroxide in the environment surrounding the sensor. As such, the membranes may preserve or improve the performance of the sensor.

Some functions of the membrane, such as regulation or limitation of analyte flux, are associated with the properties of the polymeric structure of the membrane. Further, some functions of the membrane are associated with its role as a scaffold to which functional components, such as catalytic components, can be covalently linked or otherwise bound, or in which such components can be contained. Still further, some functions of the membrane, such as protection of an underlying surface or component, are associated with the physical presence of the membrane.

According to one aspect of the invention, the membrane is formed on the sensor by in situ crosslinking of a polymer modified with a zwitterionic moiety, a non-pyridine copolymer component, and optionally another moiety (either hydrophilic or hydrophobic) that has other desirable properties, in an alcohol-buffer solution, to which an enzyme catalyst or mimic has been added. The modified polymer is made from a precursor polymer, such as polyvinylpyridine or polyvinylimidazole, containing heterocyclic nitrogen groups. When used in an electro-chemical sensor, the membrane limits the flux of an analyte reaching a sensing layer of the sensor, such as an enzyme-containing sensing layer of a "wired enzyme" electrode, and may further protect the sensing layer. These qualities of the membrane may significantly extend the linear detection range and the stability of the sensor. Additionally, the membrane, by virtue of its associated enzyme catalyst or mimic, may reduce the effect of metabolites in the vicinity of the sensor, and may thereby enhance or improve the performance of the sensor.

In the formation of the membrane according to the present invention, the components of the membrane play various roles. For example, it is believed that in the formation of a membrane according to the present invention, the zwitterionic moiety of the polymer provides a layer of crosslinking, via intermolecular electrostatic bonds, in addition to the basic crosslinking generally attributed to covalent bonds. This additional layer of crosslinking may serve to strengthen the membrane. Further, the non-pyridine copolymer component generally enhances the solubility of the polymer and may provide further desirable physical or chemical properties to the resulting polymer-based membrane. Still further, optionally, hydrophilic or hydrophobic modifiers may be used to "fine-tune" the permeability of the membrane to an analyte of interest. By way of example, hydrophilic modifiers, such as poly(ethylene glycol), hydroxyl or polyhydroxyl modifiers, may be used to enhance the biocompatibility of the polymer or the resulting membrane. Additionally, the enzyme catalysts or mimics function to regulate or to lower the concentration of various metabolites in the environment surrounding the membrane, and may thus preserve or improve the performance of the membrane in certain applications, such as the sensing of analytes in a biofluid.

Another aspect of the invention concerns the covalent incorporation of superoxide dismutase or superoxide dismutase mimics, and/or catalase or catalase mimics, and/or superoxide-dismutase/catalase catalysts or mimics, into the polymeric membrane. Generally, such incorporation is accomplished by using the biosensor membrane chemistry, which relies on crosslinks formed between glycidyl ethers (supplied by the crosslinker triglycidyl glycerol) and either amino groups (from enzymes, such as glucose oxidase) or pyridyl groups (from the poly(vinylpyridine)-based membrane polymer).

Another aspect of the invention concerns the incorporation or association of superoxide dismutase or superoxide dismutase mimics, and/or catalase or catalase mimics, and/or superoxide-dismutase/catalase catalysts or mimics, with the polymeric membrane, without resort to covalent bonds. By way of example, this incorporation or association may be achieved via ionic interactions or bonds or adsorption. Further by way of example, this incorporation or association may be achieved by providing one or more of the above-mentioned enzyme(s), mimic(s), or catalyst(s) in a vicinity of a membrane, such as a membrane on a sensing surface of a sensor, though not necessarily applying same or attaching same to the membrane.

Another aspect of the invention concerns the preparation of a substantially homogeneous, analyte-diffusion-regulating or limiting membrane for use in a biosensor, such as an amperometric glucose sensor suitable for transcutaneous use. The membrane is formed on the sensor, in situ, by applying an alcohol-buffer solution containing a crosslinker, a modified polymer, and a catalyst or catalyst mimic, over an enzyme-containing sensing layer, and allowing the solution to cure for one to two days. The crosslinker-polymer-catalyst solution may be applied to the sensing layer by placing a droplet or droplets of the solution on the sensor, by dipping the sensor into the solution, or the like. Generally, the thickness of the membrane is controlled by the concentration of the solutes, by the number of droplets of the solution applied, by the number of times the sensor is dipped in the solution, or by any combination of the these factors.

In various embodiments of the invention, the catalyst or mimic may be present in an amount of from about 0.0001 to about 30 weight percent relative to the membrane, although an amount of from about 0.001 to about 20 weight percent relative to the membrane is preferred, and an amount of from about 0.01 to about 10 weight percent relative to the membrane is more preferred. In various embodiments, corresponding or suitable amounts of catalyst or mimic may be expressed as a weight relative to a sensor or relative to a sensing surface area.

As demonstrated herein, the catalytic enhancement of a membrane-covered sensor, according to the present invention, has no negative effect on the linearity of sensor performance. Further, in an experiment involving human subjects, it was determined that catalytically enhanced, membrane-covered sensors of the present invention provided data of greater accuracy, less inaccuracy, less overall average error, and less noise than did membrane-covered sensors that were not catalytically enhanced. Still further, it was determined that no low-glucose-reading incidents occurred when catalytically enhanced, membrane-covered sensors of the present invention were employed, while several such incidents occurred when membrane-covered sensors that were not catalytically enhanced were employed. Thus, a catalyst or a mimic may be used according to the present invention to enhance or improve the performance of a sensor, such as a transcutaneous biosensor.

These and various other aspects, features and embodiments of the present invention are further described herein.

BRIEF DESCRIPTION OF THE DRAWINGS

A detailed description of various aspects, features and embodiments of the present invention is provided herein with reference to the accompanying drawings, which are briefly described below. The drawings are illustrative and are not necessarily drawn to scale. The drawings illustrate various aspects or features of the present invention and may illustrate one or more embodiment(s) or example(s) of the present invention in whole or in part. A reference numeral, letter, and/or symbol that is used in one drawing to refer to a particular element or feature may be used in another drawing to refer to a like element or feature.

FIG. 1A is an illustration of a typical structure of a section of an analyte-diffusion-limiting membrane with superoxide dismutase or a superoxide dismutase mimic covalently incorporated therein, according to the present invention. FIG. 1B is an illustration of a membrane similar to that shown in FIG. 1A, except that a specific superoxide dismutase catalyst, manganese 5,10,15,20-tetra(4-pyridyl)-21H,23H-porphine chloride, is shown covalently incorporated therein. Herein, FIGS. 1A and 1B may be collectively referred to as FIG. 1.

FIG. 2A is a schematic, side-view illustration of a portion of a two-electrode glucose sensor having a working electrode, a combined counter/reference electrode, and a dip-coated membrane that encapsulates both electrodes, according to the present invention. FIGS. 2B and 2C are schematic top- and bottom-view illustrations, respectively, of the portion of the glucose sensor of FIG. 2A. Herein, FIGS. 2A, 2B and 2C may be collectively referred to as FIG. 2.

FIG. 3 is a graph of current versus glucose concentration for sensors having glucose-diffusion-limiting membranes, according to the present invention, and for sensors lacking such membranes, based on average values.

FIG. 4 is a graph of current versus glucose concentration for sensors having superoxide-dismutase/catalase catalyst-enhanced, glucose-diffusion-limiting membranes, according to the present invention.

FIG. 5 is a graph of glucose concentration versus time for a human subject, as reported by two continuously operating, transcutaneous sensors, over a three-day period. One sensor had a conventional membrane and the other sensor had a membrane containing a superoxide-dismutase/catalase catalyst, MnTPyP. The graph also shows readings that were intermittently obtained, manually, using a conventional glucose meter, over the three-day period.

DESCRIPTION OF THE INVENTION

Biosensor Operation in Subcutaneous Environments

Various biosensors have been designed to operate partially or wholly in a living body. As these biosensors are exposed to the chemistry and biology of the body, it is now theorized that various chemical and biological factors may complicate their operation or performance. For example, an implanted biosensor is completely enclosed within a body and remains within the body for a period varying from weeks to years. Such an implanted sensor may have long-term effects, such as the long-term effects of the body's immunologic reaction to the sensor as a foreign body. A transcutaneous biosensor is much less invasive, as only a portion of the sensor spans the cutaneous barrier of a living body, i.e., a portion that extends from the external surface of the body into the interstitial fluid space within the cutaneous layer, and that portion only remains in the interstitial fluid space for a period on the order of about three to about five days. Even within this relatively short period, however, the early phases of the immune system response to the inserted portion of the sensor are activated. In these early phases of the immune system response, neutrophils are quickly recruited to the subcutaneous space, whereupon they metabolically consume glucose and produce enzymes and oxidative metabolites, all of which may have significant effects on sensor performance.

Neutrophils, the main phagocytic leukocytes of the blood, recognize foreign surfaces almost immediately and are quickly recruited to the site of a foreign body intrusion. At the foreign body site, neutrophils release destructive enzymes and oxidants to damage the intruder, while at the same time, they attempt to physically engulf and devour the intruder. The released oxidants are derived from hydrogen peroxide, superoxide radicals, nitric oxide and chloride, the former two of which may act to attract further neutrophils and thereby accelerate their own respective accumulation. The released oxidants include hydroxyl radicals, formed through the reaction of hydrogen peroxide with reduced transition metal cations or their complexes; peroxy-nitrous acid, formed of nitric oxide and superoxide radicals; and hypochlorite, formed of hydrogen peroxide and chloride. The resulting oxidant cocktail is strong, able to oxidize most organic chemicals and to provide a local antiseptic effect.

Neutrophils may have several effects on a glucose sensor and its performance in the body. For example, newly recruited neutrophils are in the midst of an "oxidative burst" that is characterized by high metabolic activity. Metabolically active cells in high concentration are likely to deplete the local environment of the glucose they consume for energy. Local glucose depletion may compromise the value of glucose sensing data, as however accurate the data may be in a very local sense, the data may not be reflective of the clinically relevant level of glucose in the bloodstream. It is now theorized that accumulated neutrophils, in their attempt to engulf the sensing surface, may physically cover it to the extent that the sensor no longer has effective contact with the surrounding interstitial fluid. This theory is considered a possible explanation for low glucose readings that occur during periods of stillness, such as sleep, and the recovery of those glucose readings to normal upon body movement that may either disturb the accumulated neutrophils, or more generally, stir the stagnant interstitial fluid surrounding the sensor. Further, in terms of the panoply of effects that neutrophils may have on glucose sensor data, it is now theorized that the oxidants released by the neutrophils in an immune system response may have direct disrupting effects on the electrochemistry of the sensor.

An immune system response, such as that described above, typically results in inflammation. One particular approach to controlling inflammation associated with the presence of long-term device implants, such as cardiac stents, replacement joints and the like, involves the use of superoxide dismutase (SOD) to consume accumulated superoxide. Superoxide, a product of neutrophil metabolism, as well as an attractor of neutrophils and other cells of the immune system, is a highly reactive species that gives rise to other oxygen metabolites. Superoxide itself is implicated in the pathogenesis of numerous processes, including the generation of nitric oxide, which has further deleterious effects on the vascular endothelium. The reaction catalyzed by the SOD enzyme, known as "dismutation" of superoxide, consumes two superoxide ions and two hydrogen ions to yield molecular oxygen and hydrogen peroxide, per the following reaction: $O_2^-$ +

$O_2^- + 2H^+ \rightarrow O_2 + H_2O_2$. As such, the SOD enzyme would appear to be capable of catalyzing the removal of at least some of the superoxide that is present at a site of neutrophil metabolism.

The SOD enzyme has actually been shown to reduce inflammation (Chan et al., Protective Effects of Liposome-Entrapped Superoxide Dismutase on Posttraumatic Brain Edema, Ann. Neurol. 1987; 21, 540-547), presumably by reducing local concentrations of superoxide (Chan et al., *Free Fatty Acids, Oxygen Free Radicals, and Membrane Alterations in Brain Ischemia and Injury, in Cerebrovascular Diseases*, edited by Plum et al., Raven Press, New York 1985, 161-171). This ubiquitous enzyme plays a widespread role in physiological homeostasis. The SOD enzyme includes a manganese-containing form of the enzyme that is found in mitochondria, a copper- or zinc-containing form of the enzyme that is found in plasma and in extracellular fluid, and an iron-containing form of the enzyme that is found in anaerobic prokaryotes (D. P. Riley, Functional mimics of superoxide dismutase enzymes as therapeutic agents, Chem. Rev. 1999, 99, 2573-2587).

Non-proteinaceous, mimics of superoxide dismutase (SOD mimics) have also been shown to reduce inflammation (Weiss et al., Manganese-Based Superoxide Dismutase Mimetics Inhibit Neutrophil Infiltration In-Vivo, J. Biol. Chem. 1996; 271, 26149-26156). For example, a class of manganese- or iron-complexes of nitrogen-containing, fifteen-membered, macrocyclic ligands has recently been shown to have the catalytic activity of SOD, and to be effective, when attached to the surface of small plastic implants, in reducing the inflammation caused by implantation (U.S. Pat. No. 6,525,041 of Neumann et al., filed on Mar. 14, 1996; Published PCT Application, International Publication No. WO 00/72893 A2 of Ornberg et al., filed on May 26, 2000; and Udipi et al., J. Biomed. Mater. Res. 2000, 51(4), 549-560). Articles providing an overview of SOD mimics include Riley, Functional Mimics of Superoxide Dismutase Enzymes as Therapeutic Agents, Chemical Reviews 1999, 99, 2573-2587) and Salvemini et al., Superoxide Dismutase Mimetics, Pulmonary Pharmacology and Therapeutics 2002, 15, 439-447), and patents disclosing such mimics include U.S. Pat. Nos. 5,610,293 and 6,084,093 of Riley et al., filed on May 16, 1995, and U.S. Pat. No. 6,214,817 of Riley et al., filed on Sep. 16, 1999.

Yet another enzyme, catalase, and non-proteinaceous mimics of catalase, may have ameliorative effects on inflammation. Like superoxide, hydrogen peroxide is a product of neutrophil metabolism that attracts further neutrophils. The reaction catalyzed by catalase, namely, the decomposition of hydrogen peroxide, consumes one molecule of hydrogen peroxide to produce two molecules of water and one molecule of oxygen gas. As such, the catalase enzyme, and mimics thereof, would appear to be capable of catalyzing the removal of at least some of the hydrogen peroxide that is present at a site of neutrophil metabolism.

Some non-proteinaceous compounds catalyze both superoxide dismutation and hydrogen peroxide decomposition. These compounds may be referred to as "superoxide dismutase/catalase mimics." Eukarion, Inc. of Bedford, Mass. has developed such mimics, or what it calls "synthetic catalytic scavengers," and provides references to publications concerning same (such as S. R. Doctrow et al., "Salen manganese complexes" combined superoxide dismutase/catalase mimics with broad pharmacological efficacy, Advances in Pharmacology 1996, 38, 247-269) on its website (http://www.eukarion.com/). Patents and a patent application that disclose compounds having such dual catalytic activity include U.S. Pat. Nos. 5,202,317 and 5,217,966 of Bruice, filed on Sep. 13, 1990 and Jan. 17, 1992, respectively; U.S. Pat. No. 6,403,788 of Meunier et al., filed on Jul. 11, 2000, U.S. Pat. No. 6,541,490 of Campbell et al., filed on Nov. 27, 2000, and U.S. Pat. Nos. 6,573,257 and 6,589,948 of Malfroy-Camine et al., filed on Apr. 4, 2000 and Nov. 28, 2000, respectively; and U.S. Patent Application Publication No. U.S. 2003/0118577 A1 of Weill et al., filed on Feb. 3, 2003.

According to the present invention, various catalysts are used in connection with biosensors that are used to measure analyte concentration, such as glucose concentration, in interstitial fluid with which the biosensor is in contact. The catalysts are used to catalyze the removal of at least some of the harmful metabolites, such as superoxide or hydrogen peroxide, that may be present at in the vicinity of the biosensor, a site of neutrophil metabolism. As demonstrated herein, biosensors equipped with such catalysts are better able to handle the complex and variable biological environment that is associated with in vivo biosensing. While such biosensors are for the most part described in relation to transcutaneous, amperometric glucose sensors herein, it will be understood that the present invention encompasses the use of catalysts in connection with other analyte sensors.

Various Conventions and Terms

In the description of the invention herein, it will be understood that a word appearing in the singular encompasses its plural counterpart, and a word appearing in the plural encompasses its singular counterpart, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are now described and/or defined to facilitate an understanding of the invention. The terms in quotation marks are described and/or defined as set forth below.

"Alkenyl" refers to an unsaturated, linear or branched aliphatic hydrocarbon having at least one carbon-carbon double bond. Examples of alkenyl groups include ethenyl, 1-propenyl, 2-propenyl, 1-butenyl, 2-methyl-1-propenyl, and the like.

"Alkoxy" refers to an alkyl group joined to the remainder of the structure by an oxygen atom. Examples of alkoxy groups include methoxy, ethoxy, n-propoxy, isopropoxy, butoxy, tert-butoxy, and the like. Unless otherwise noted, the term "alkoxy" includes both alkoxy and cycloalkoxy groups.

"Alkyl" refers to linear or branched, saturated aliphatic hydrocarbons. Examples of alkyl groups include methyl, ethyl, n-propyl, isopropyl, n-butyl, tert-butyl and the like. Unless otherwise noted, the term "alkyl" includes both alkyl and cycloalkyl groups.

A "biofluid" is any bodily fluid or derivative thereof in which an analyte such as glucose can be measured, for example, blood, interstitial fluid, plasma, dermal fluid, sweat, and tears.

"Catalase" is an enzyme that catalyzes the decomposition of hydrogen peroxide.

A "catalyst" refers to an agent that facilitates a chemical reaction. An enzyme is a proteinaceous catalyst. A mimic of an enzyme is a non-proteinaceous catalyst that facilitates the same reaction as does the enzyme.

A "counter electrode" includes both (a) a counter electrode and (b) a counter electrode that also functions as a reference electrode (i.e., a counter/reference electrode).

A "crosslinker" is a molecule that contains at least two reactive groups capable of linking at least two molecules together, or linking at least two portions of the same molecule together. Linking of at least two molecules is called intermolecular crosslinking; linking of at least two portions of the same molecule is called intramolecular crosslinking. A crosslinker having more than two reactive groups may be capable of coincidental intermolecular and intramolecular crosslinkings.

An "electrochemical sensor" is a device configured to detect the presence of or measure the concentration or amount of an analyte in a sample via electrochemical oxidation or reduction reactions. Typically, these reactions are transduced to an electrical signal that is correlated to an amount or concentration of analyte.

A "heterocyclic nitrogen group" refers to a generally carbon-based cyclic structure containing an sp2 hybridized nitrogen integrated within a ring of the structure.

"Interstitial fluid," also known as "extracellular fluid," refers to the fluid in the body that fills the space between cells. This fluid is distinct from fluid contained within the vessels of circulatory system, which is referred to as "plasma." A transcutaneously-placed glucose sensor is exposed to interstitial fluid. Glucose levels in the interstitial fluid and plasma (as from a conventional capillary blood sample) are in equilibrium, although a rapid or local change in one may not be immediately reflected in the other.

A "low-glucose-reading incident" refers to an occurrence of a glucose or blood glucose reading that is lower than expected and is considered spurious to the extent it may not truly reflect the systemic blood glucose level.

A "membrane solution" is a solution that comprises components for crosslinking and forming the membrane, such as a modified polymer containing heterocyclic nitrogen groups, a crosslinker, and a buffer or an alcohol-buffer mixed solvent. A "catalyst-enhanced membrane solution" is a membrane solution that includes an enzyme catalyst or a mimic thereof.

A "mimic" or "non-proteinaceous mimic" both refer to a non-proteinaceous compound that has a catalytic activity like that of a known enzyme. The non-proteinaceous compound may comprise a metallic component and an organic component, wherein a metal ion or atom of the metallic component and a nonmetallic ion, molecule, portion, or ligand of the organic component form a union. Such a non-proteinaceous compound may be referred to as a metal-nonmetallic or nonmetallic-metal compound, a metal-organic or organic-metal compound, and/or the like, and is sometimes referred to as an organometallic compound, as that term is often loosely used or as that term is strictly used. When the union is coordinative or complexing in nature, such a non-proteinaceous compound may be referred to as a coordination compound, a complex compound, a metal-nonmetallic or nonmetallic-metal complex or coordination compound, a metal-organic complex or coordination compound, and/or the like. When the union is in the form of a direct metal to carbon attachment, whether of a coordinative, complexing, or other nature, the non-proteinaceous compound may be referred to as an organometallic compound, as that term is strictly used. The non-proteinaceous compound may comprise any suitable metal, such as any suitable metal in any of Groups 3 through 12 (new notation) or IB through VIIIB (CAS notation) of the Periodic Table of the Elements or any suitable metal in the family of transition metals, such as manganese, iron, copper, or zinc, merely by way of example.

"Peroxidase" is an enzyme that catalyzes the decomposition of hydrogen peroxide.

"Polyvinylimidazole" refers to poly(1-vinylimidazole), poly(2-vinylimidazole), or poly(4-vinylimidazole).

"Polyvinylpyridine" refers to poly(4-vinylpyridine), poly (3-vinylpyridine), or poly(2-vinylpyridine), as well as any copolymer of vinylpyridine and a second or a third copolymer component.

A "precursor polymer" refers to a starting polymer before any of various modifier groups are attached to form a modified polymer.

A "reactive group" is a functional group of a molecule that is capable of reacting with another compound to couple or covalently bind at least a portion of that other compound to the molecule. Reactive groups include carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. Activated esters, as understood in the art, generally include esters of succinimidyl, benzo-triazolyl, or aryl substituted by electron-withdrawing groups such as sulfo, nitro, cyano, or halo groups; or carboxylic acids activated by carbodiimides.

A "redox mediator" is an electron-transfer agent for carrying electrons between an analyte, an analyte-reduced or analyte-oxidized enzyme, and an electrode, either directly, or via one or more additional electron-transfer agents. A redox mediator that includes a polymeric backbone may also be referred to as a "redox polymer."

A "reference electrode" includes both a) a reference electrode and b) a reference electrode that also functions as a counter electrode (i.e., a counter/reference electrode), unless otherwise indicated.

A "substituted" functional group (e.g., substituted alkyl, alkenyl, or alkoxy group) includes at least one substituent selected from the following: halogen, alkoxy, mercapto, aryl, alkoxycarbonyl, alkylaminocarbonyl, dialkylaminocarbonyl, $-OH$, $-NH_2$, alkylamino, dialkyl-amino, trialkylammonium, alkanoylamino, arylcarboxamido, hydrazino, alkylthio, alkenyl, and reactive groups.

"Superoxide dismutase" (SOD) refers to an enzyme that catalyzes the dismutation of superoxide.

A "superoxide-dismutase/catalase catalyst" refers to a catalyst, whether an enzyme or a mimic or another agent, that possesses the catalytic activity of one of superoxide dismutase and catalase, to any degree, or the catalytic activities of both superoxide dismutase and catalase, to any degree. The term, superoxide-dismutase/catalase catalyst, encompasses a preferred embodiment in which an agent that catalyzes the dismutation of superoxide also catalyzes the decomposition of hydrogen peroxide, and vice versa. The term, superoxide-dismutase/catalase catalyst, also encompasses embodiments in which an agent catalyzes the dismutation of superoxide, but not the decomposition of hydrogen peroxide, and embodiments in which an agent catalyzes only the decomposition of hydrogen peroxide, but not the dismutation of superoxide.

A "superoxide-dismutase/catalase mimic" refers to a mimic that possesses the catalytic activity of one of superoxide dismutase and catalase, to any degree, or the catalytic activities of both superoxide dismutase and catalase, to any degree. The term, superoxide-dismutase/catalase mimic, encompasses a preferred embodiment in which an agent that catalyzes the dismutation of superoxide also catalyzes the decomposition of hydrogen peroxide, and vice versa. The term, superoxide-dismutase/catalase mimic, also encompasses embodiments in which an agent catalyzes the dismutation of superoxide, but not the decomposition of hydrogen peroxide, and embodiments in which an agent catalyzes the decomposition of hydrogen peroxide, but not the dismutation of superoxide.

"Transcutaneous" refers to the location or state of a biosensor when a portion of the biosensor is placed across or crosses the cutaneous layer, such that one portion of the biosensor is external to the body, and another portion of the biosensor, including the sensing layer, is in the subcutaneous space, and in contact with interstitial fluid.

The catalysts described above may be associated with a membrane, and particularly with a membrane that forms part of a biosensor. Such membranes are now described.

Heterocyclic-Nitrogen Containing Polymers

In general, the exemplary membranes of the present invention are formed by crosslinking a modified polymer containing heterocyclic nitrogen groups in an alcohol-buffer mixed solvent and allowing the membrane solution to cure over time. The polymer comprises poly(heterocyclic nitrogen-containing constituent) as a portion of its backbone and additional elements, including a zwitterionic moiety, a hydrophobic moiety, and optionally, a biocompatible moiety. The resulting membrane is capable of regulating or limiting the flux of an analyte from one space, such as a space associated with a biofluid, to another space, such as space associated with an enzyme-containing sensing layer. An amperometric glucose sensor constructed of a wired-enzyme sensing layer and a glucose-diffusion-limiting layer of the present invention is very stable and has a large linear detection range.

The polymer of the present invention has the following general formula, Formula 1a:

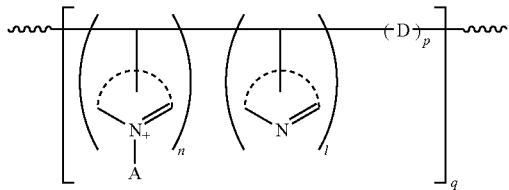

Formula 1a wherein the horizontal line represents a polymer backbone; A is an alkyl group substituted with a water soluble group, preferably a negatively charged group, such as sulfonate, phosphate, or carboxylate, and more preferably, a strong acid group such as sulfonate, so that the quaternized heterocyclic nitrogen to which it is attached is zwitterionic; D is a copolymer component of the polymer, as further described below; each of n, l, and p is independently an average number of an associated polymer unit or polymer units shown in the closest parentheses to the left; and q is a number of a polymer unit or polymer units shown in the brackets.

The heterocyclic nitrogen groups of Formula 1a include pyridine, imidazole, oxazole, thiazole, pyrazole, or any derivative thereof. Preferably, the heterocyclic nitrogen groups are independently vinylpyridine, such as 2-, 3-, or 4-vinylpyridine, or vinylimidazole, such as 1-, 2-, or 4-vinylimidazole. More preferably, the heterocyclic nitrogen groups are independently 4-vinylpyridine, such that the more preferable polymer is a derivative of poly(4-vinylpyridine). An example of such a poly(4-vinylpyridine) of the present invention (wherein A, D, n, l, p and q are as described above in relation to Formula 1a) has the general formula, Formula 1b, as set forth below.

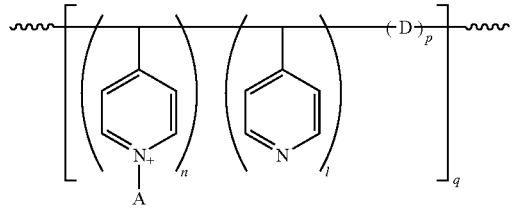

Formula 1b

While the polymer of the present invention has the general Formula 1a or Formula 1b above, it should be noted that when A is a strong acid, such as an acid stronger than carboxylic acid, the D component is optional, such that p may equal zero. Such a polymer, wherein A is a strong acid and the heterocyclic nitrogen groups, n, l and q are all as described above, has the general formula, Formula 1c, as set forth below.

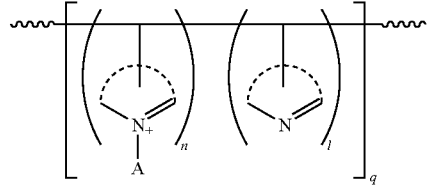

Formula 1c

Sulfonate and fluorinated carboxylic acid are examples of suitably strong acids. It is believed that when A is a sufficiently strong acid, the heterocyclic nitrogen to which it is attached becomes zwitterionic and thus capable of forming intermolecular electrostatic bonds with the crosslinker during membrane formation. It is believed that these intermolecular electrostatic bonds provide another level of crosslinking, beyond the covalent bonds typical of crosslinking, and thus make the resulting membrane stronger. As a result, when A is a suitably strong acid, the D component, which is often a strengthening component such as styrene, may be omitted from the polymers of Formulas 1a and 1b above. When A is a weaker acid, such that the heterocyclic nitrogen is not zwitterionic or capable of forming intermolecular electrostatic bonds, the polymer of the present invention does include D, as shown in Formulas 1a and 1b above.

Examples of A include sulfopropyl, sulfobutyl, carboxypropyl, and carboxypentyl. In one embodiment of the invention, group A has the formula -L-G, where L is a C2-C12 linear or branched alkyl linker optionally and independently substituted with an aryl, alkoxy, alkenyl, alkynyl, —F, —Cl, —OH, aldehyde, ketone, ester, or amide group, and G is a negatively charged carboxy or sulfonate group. The alkyl portion of the substituents of L have 1-6 carbons and are preferably an aryl, —OH or amide group.

A can be attached to the heterocyclic nitrogen group via quaternization with an alkylating agent that contains a suitable linker L and a negatively charged group G, or a precursor group that can be converted to a negatively charged group G at a later stage. Examples of suitable alkylating agents include 2-bromoethanesulfonate, propanesultone, butanesultone, bromoacetic acid, 4-bromobutyric acid and 6-bromohexanoic acid. Examples of alkylating agents containing a precursor group include ethyl bromoacetate and methyl 6-bromohexanoate. The ethyl and methyl ester groups of these precursors can be readily converted to a negatively charged carboxy group by standard hydrolysis.

Alternatively, A can be attached to the heterocyclic nitrogen group by quaternizing the nitrogen with an alkylating agent that contains an additional reactive group, and subsequently coupling, via standard methods, this additional reactive group to another molecule that contains a negatively charged group G and a reactive group. Typically, one of the reactive groups is an electrophile and the other reactive group is a nucleophile. Selected examples of reactive groups and the linkages formed from their interactions are shown in Table 1.

TABLE 1

Examples of Reactive Groups and Resulting Linkages

| First Reactive Group | Second Reactive Group | Resulting Linkage |
|---|---|---|
| Activated Ester* | Amine | Amide |
| Acrylamide | Thiol | Thioether |
| Acyl Azide | Amine | Amide |
| Acyl Halide | Amine | Amide |
| Carboxylic Acid | Amine | Amide |
| Aldehyde or Ketone | Hydrazine | Hydrazone |
| Aldehyde or Ketone | Hydroxyamine | Oxime |
| Alkyl Halide | Amine | Alkylamine |
| Alkyl Halide | Carboxylic acid | Ester |
| Alkyl Halide | Imidazole | Imidazolium |
| Alkyl Halide | Pyridine | Pyridinium |
| Alkyl Halide | Alcohol/phenol | Ether |
| Alkyl Halide | Thiol | Thioether |
| Alkyl Sulfonate | Thiol | Thioether |
| Alkyl Sulfonate | Pyridine | Pyridinium |
| Alkyl Sulfonate | Imidazole | Imidazolium |
| Alkyl Sulfonate | Alcohol/phenol | Ether |
| Anhydride | Alcohol/phenol | Ester |
| Anhydride | Amine | Amide |
| Aziridine | Thiol | Thioether |
| Aziridine | Amine | Alkylamine |
| Aziridine | Pyridine | Pyridinium |
| Epoxide | Thiol | Thioether |
| Epoxide | Amine | Alkylamine |
| Epoxide | Pyridine | Pyridinium |
| Halotriazine | Amine | Aminotriazine |
| Halotriazine | Alcohol | Triazinyl ether |
| Imido ester | Amine | Amidine |
| Isocyanate | Amine | Urea |
| Isocyanate | Alcohol | Urethane |
| Isothiocyanate | Amine | Thiourea |
| Maleimide | Thiol | Thioether |
| Sulfonyl | halide Amine | Sulfonamide |

*Activated esters, as understood in the art, generally include esters of succinimidyl, benzotriazolyl, or aryl substituted by electron-withdrawing groups such as sulfo, nitro, cyano, or halo; or carboxylic acids activated by carbodiimides.

By way of example, A may be attached to the heterocyclic nitrogen groups of the polymer by quaternizing the heterocyclic nitrogens with 6-bromohexanoic acid and subsequently coupling the carboxy group to the amine group of 3-amino-1-propanesulfonic acid in the presence of a carbodiimide coupling agent.

D is a component of a poly(heterocyclic nitrogen-co-D) polymer of Formula 1a or 1b. Examples of D include phenylalkyl, alkoxystyrene, hydroxyalkyl, alkoxyalkyl, alkoxycarbonylalkyl, and a molecule containing a poly(ethylene glycol) or polyhydroxyl group. Some poly(heterocyclic nitrogen-co-D) polymers suitable as starting materials for the present invention are commercially available. For example, poly(2-vinylpyridine-co-styrene), poly(4-vinyl-pyridine-co-styrene) and poly(4-vinylpyridine-co-butyl methacrylate) are available from Aldrich Chemical Company. Other poly(heterocyclic nitrogen-co-D) polymers can be readily synthesized by one skilled in the art of polymer chemistry using well-known methods. Preferably, D is a styrene or a C1-C18 alkyl methacrylate component of a polyvinylpyridine-poly-D, such as (4-vinylpyrine-co-styrene) or poly(4-vinylpyridine-co-butyl methacrylate), more preferably, the former. D may contribute to various desirable properties of the membrane including, but not limited to, hydrophobicity, hydrophilicity, solubility, biocompatibility, elasticity and strength. D may be selected to optimize or "fine-tune" a membrane made from the polymer in terms of its permeability variously to an analyte and/or its non-permeability to an undesirable, interfering component.

The letters n, l, and p designate, respectively, an average number of each copolymer component in each polymer unit. The letter q is one for a block copolymer or a number greater than one for a copolymer with a number of repeating polymer units. By way of example, the q value for a polymer of the present invention may be $\geq$ about 950, where n is 1, l is 8 and p is 1. The letter q is thus related to the overall molecular weight of the polymer. Preferably, the average molecular weight of the polymer is above about 50,000; more preferably above about 200,000, most preferably above about 1,000,000.

The polymer of the present invention may comprise a further, optional copolymer, wherein the polymer backbone, A, D, n, l, p and q are as described above in relation to Formulas 1a-1c; m is an average number of an associated polymer unit or polymer units shown in the closest parentheses to the left; and B is a modifier, as shown in the general formula, Formula 2a, as set forth below.

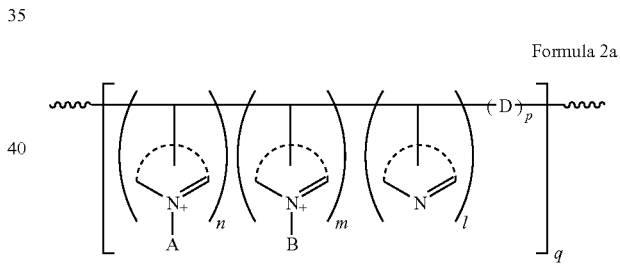

Formula 2a

When the heterocyclic nitrogen groups are 4-substituted pyridine, as is preferred, the polymer of the present invention is derivative of poly(4-vinylpyridine) and has the general formula, Formula 2b, set forth below.

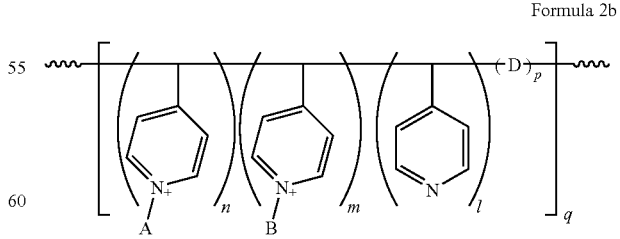

Formula 2b

Further, when A is a suitably strong acid, as described above, the D copolymer is optional, in which case the polymer of the present invention has the general formula, Formula 2c, as set forth below.

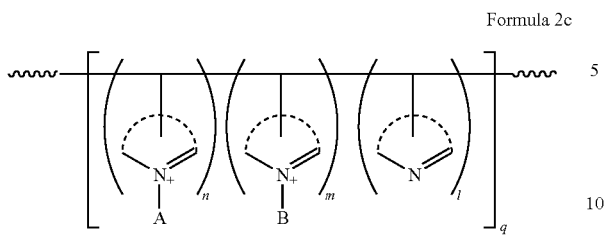

Formula 2c

In any of Formulas 2a-2c, B is a modifier group that may add any desired chemical, physical or biological properties to the membrane. Such desired properties include analyte selectivity, hydrophobicity, hydrophilicity, elasticity, and biocompatibility. Examples of modifiers include the following: negatively charged molecules that may minimize entrance of negatively charged, interfering chemicals into the membrane; hydrophobic hydrocarbon molecules that may increase adhesion between the membrane and sensor substrate material; hydrophilic hydroxyl or polyhydroxy molecules that may help hydrate and add biocompatibility to the membrane; silicon polymers that may add elasticity and other properties to the membrane; and poly(ethylene glycol) constituents that are known to increase biocompatibility of biomaterials (Bergstrom, et al., J. Biomed. Mat. Res. 26, 779 (1992)). Further examples of B a metal chelator, such as a calcium chelator, and other biocompatible materials. A poly(ethylene glycol) suitable for biocompatibility modification of the membrane generally has a molecular weight ranging from about 100 to about 20,000, preferably, from about 500 to about 10,000, and more preferably, from about 1,000 to about 8,000.

The modifier B can be attached to the heterocyclic nitrogens of the polymer directly or indirectly. In direct attachment, the heterocyclic nitrogen groups may be reacted with a modifier containing an alkylating group. Suitable alkylating groups include alkyl halide, epoxide, aziridine, and sulfonate esters. In indirect attachment, the heterocyclic nitrogens of the polymer may be quaternized with an alkylating agent having an additional reactive group, and then attached to a molecule having a desired property and a suitable reactive group.

As described above, the B-containing copolymer is optional in the membrane of the present invention, such that when m of Formula 2a-2c is zero, the membrane has the general formula of Formula 1a-1c, respectively. The relative amounts of the four copolymer components, the heterocyclic nitrogen group containing A, the optional heterocyclic nitrogen group containing B, the heterocyclic nitrogen group, and D, may be conveniently expressed as percentages, as follows: $[n/(n+m+l+p)] \times 100\%$, $[m/(n+m+l+p)] \times 100\%$, $[l/(n+m+l+p)] \times 100\%$, and $[p/(n+m+l+p)] \times 100\%$, respectively. Suitable percentages are 1-25%, 0-15% (when the B-containing heterocyclic nitrogen group is optional) or 1-15%, 20-90%, and 0-50% (when D is optional) or 1-50%, respectively, and preferable percentages are 5-20%, 0-10% (when the B-containing heterocyclic nitrogen group is optional) or 1-10%, 60-90%, and 5-20%, respectively.

Specific examples of suitable polymers have the general formulas, Formulas 3-6, shown below.

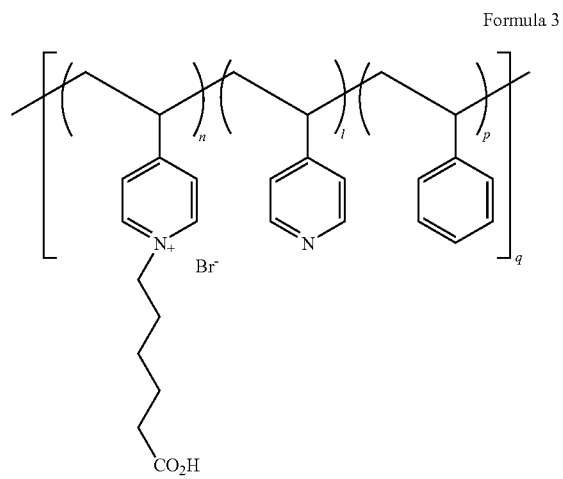

Formula 3

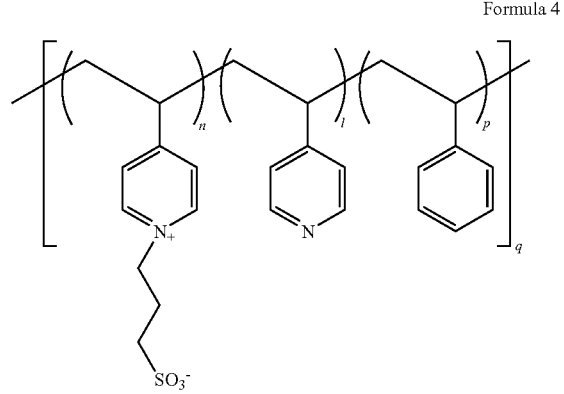

Formula 4

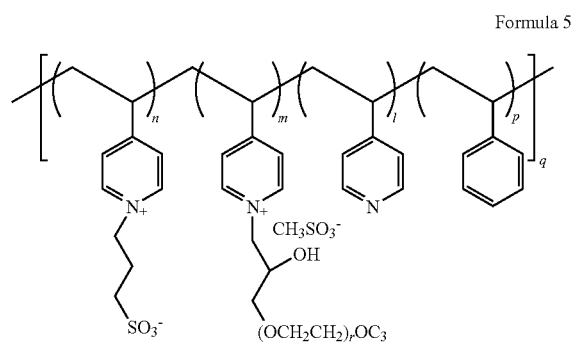

Formula 5

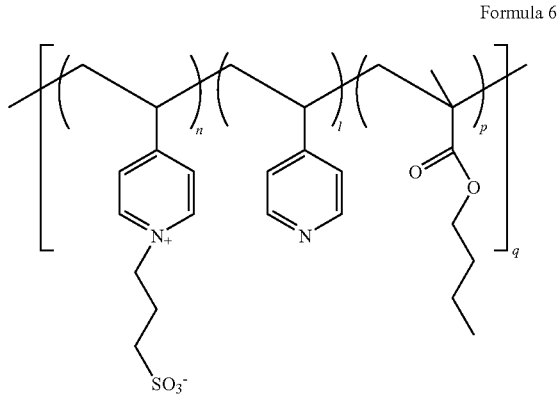

Formula 6

EXAMPLES OF SYNTHESES OF POLYVINYLPYRIDINE POLYMERS

Examples showing the syntheses of various polyvinylpyridine polymers according to the present invention are provided below. Numerical descriptors provided are approximate.

Synthesis Example 1

The Polymer of Formula 3

By way of illustration, an example of the synthesis of a polymer of Formula 3 above, is now provided. A solution of poly(4-vinylpyridine-co-styrene) (~10% styrene content) (20 g, Aldrich) in 100 mL of dimethyl formamide (DMF) at 90° C. was stirred and 6-bromohexanoic acid (3.7 g) in 15-20 mL of DMF was added. The resulting solution was stirred at 90° C. for 24 hours and then poured into 1.5 L of ether, whereupon the solvent was decanted. The remaining gummy solid was dissolved in MeOH (150-200 mL) and suction-filtered through a medium-pore, fritted funnel to remove any undissolved solid. The filtrate was added slowly to rapidly stirred ether (1.5 L) in a beaker. The resulting precipitate was collected by suction filtration and dried at 50° C. under high vacuum for two days. The polymer had the following parameters: $[n/(n+l+p)] \times 100\% \approx 70\%$; $[l/(n+l+p)] \times 100\% \approx 80\%$; and $[p/(n+l+p)] \times 100\% \approx 10\%$.

Synthesis Example 2

The Polymer of Formula 5

By way of illustration, an example of the synthesis of a polymer of Formula 5 above, is now provided. A solution of poly(4-vinylpyridine-co-styrene) (~10% styrene) (20 g, Aldrich) in 100 mL of anhydrous DMF at 90° C. was stirred, methanesulfonic acid (about 80 mg) was added, and then 2 g of methoxy-PEG-epoxide (molecular weight 5,000) (Shearwater Polymers, Inc.) in 15-20 mL of anhydrous DMF was added. The solution was stirred at 90° C. for 24 hours and 1,3-Propane sultone (2.32 g) in 10 mL of anhydrous DMF was added. The resulting solution was continuously stirred at 90° C. for 24 hours, and then cooled to room temperature and poured into 800 mL of ether. The solvent was decanted and the remaining precipitate was dissolved in hot MeOH (~200 mL), suction-filtered, precipitated again from 1 L of ether, and then dried at 50° C. under high vacuum for 48 hours. The resulting polymer has the following parameters: $[n/(n+m+l+p)] \times 100\% \approx 10\%$; $[m/(n+m+l+p)] \times 100\% \approx 10\%$; $[l/(n+m+l+p)] \times 100\% \approx 70\%$; and $[p/(n+m+l+p)] \times 100\% \approx 10\%$.

Synthesis Example 3

A Polymer having a Polyhydroxy Modifier B

By way of illustration, an example of the synthesis of a polymer having a polyhydroxy modifier B, as schematically illustrated below, is now provided. Various polyhydroxy compounds are known for having biocompatibility properties. (U.S. Pat. No. 6,011,077 of Muller, filed on Sep. 12, 1997.) The synthesis below illustrates how a modifier group having a desired property may be attached to the polymer backbone via a linker.

Synthesis of a Polymer Having a Polyhydroxy Modifier B

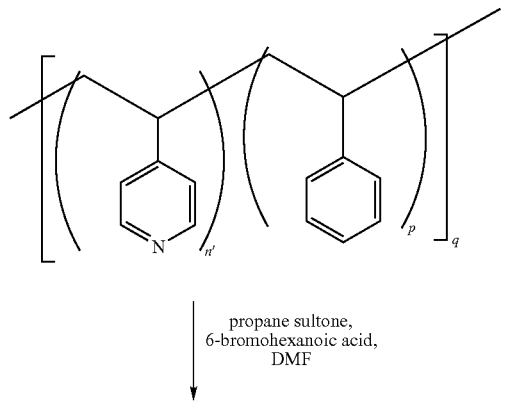

propane sultone,
6-bromohexanoic acid,
DMF

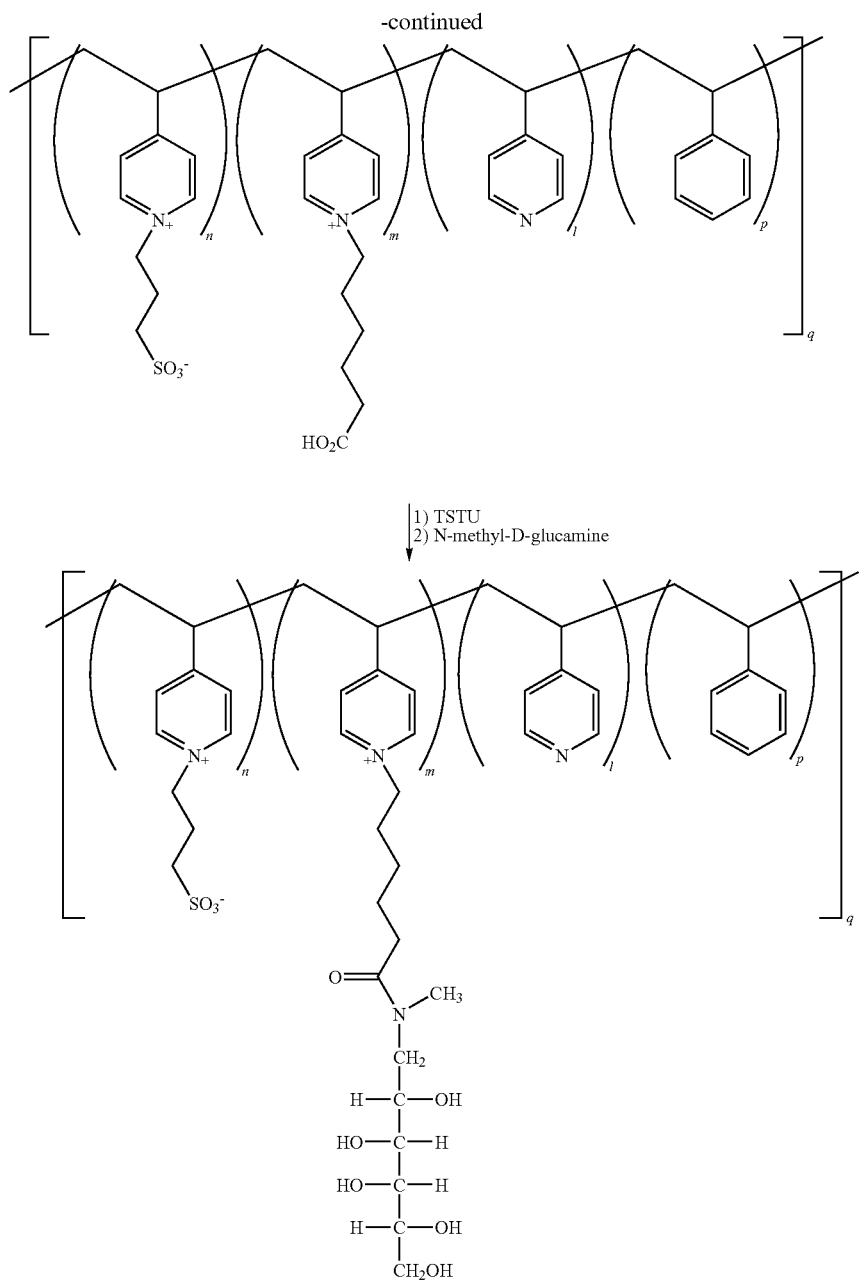

In this synthesis, 1,3-propane sultone (0.58 g, 4.8 mmoles) and 6-bromohexanoic acid (1.85 g, 9.5 mmoles) was added to a solution of poly(4-vinylpyridine-co-styrene) (~10% styrene) (10 g) dissolved in 60 mL of anhydrous DMF. The resulting solution was stirred at 90° C. for 24 hours and then cooled to room temperature. O-(N-succinimidyl)-N,N,N',N'-tetramethyluronium tetrafluoroborate (TSTU) (2.86 g, 9.5 mmoles) and N,N-diisopropylethylamine (1.65 mL, 9.5 mmoles) was then added in succession to the solution. After the solution was stirred for 5 hours, N-methyl-D-glucamine (2.4 g, 12.4 mmoles) was added and the resulting solution was stirred at room temperature for 24 hours. The solution was poured into 500 ml of ether and the precipitate was collected by suction filtration. The collected precipitate was then dissolved in MeOH/H$_2$O and the resulting solution was subjected to ultra membrane filtration using the same MeOH/H$_2$O solvent to remove small molecules. The dialyzed solution was evaporated to dryness to give a polymer with the following parameters: [n/(n+m+l+p)]×100%≈10%; [m/(n+m+l+p)]×100%≈10%; [l/(n+m+l+p)]×100%≈70%; and [p/(n+m+l+p)]×100%≈10%.

Crosslinkers

Crosslinkers of the present invention are molecules having at least two reactive groups, such as bi-, tri-, or tetra-functional groups, capable of reacting with the heterocyclic nitrogen groups, pyridine groups, or other reactive groups contained on A, B, or D of the polymer. Preferably, the reactive groups of the crosslinkers are slow-reacting alkylating groups that can quaternize the heterocyclic nitrogen groups (such as pyridine groups) of the polymer. Suitable alkylating groups include derivatives of poly(ethylene glycol) or poly(propylene glycol), epoxide (glycidyl group), aziridine, alkyl halide, and sulfonate esters. Alkylating groups of the crosslinkers are preferably glycidyl groups. Preferably, glycidyl crosslinkers have a molecular weight ranging from about 200 to about 2,000 and are water soluble or soluble in a water-miscible solvent, such as an alcohol. Examples of suitable crosslinkers include poly(ethylene glycol) diglycidyl ether with a molecular weight ranging about 200 to about 600, N,N-diglycidyl-4-glycidyloxyaniline, and tryglycidyl glycerol.

It is desirable to have a slow crosslinking reaction during the dispensing of membrane solution so that the membrane coating solution has a reasonable pot-life for large-scale manufacture. A fast crosslinking reaction results in a coating solution of rapidly changing viscosity, which renders coating difficult. Ideally, the crosslinking reaction is slow during the dispensing of the membrane solution, and accelerated during the curing of the membrane at ambient temperature, or at an elevated temperature where possible.

Membrane Formation and Sensor Fabrication

An example of a process for producing a membrane of the present invention is now described. In this example, the polymer of the present invention and a suitable crosslinker are dissolved in a buffer-containing solvent, typically a buffer-alcohol mixed solvent, to produce a membrane solution. Preferably, the buffer has a pH in the range of about 7.5 to about 9.5 and the alcohol is ethanol. More preferably, the buffer is a 10 mM (2-(4-(2-hydroxyethyl)-1-piperazine)-ethanesulfonate) (HEPES) buffer (pH 8) and the ethanol to buffer volume ratio is from about 95 to 5 to about 0 to 100. Only a small amount of buffer is necessary for the crosslinking chemistry, especially if an epoxide or aziridine crosslinker is used. The amount of solvent needed to dissolve the polymer and the crosslinker may vary depending on the nature of the polymer and the crosslinker. For example, a higher percentage of alcohol may be required to dissolve a relatively hydrophobic polymer and/or crosslinker.

The ratio of polymer to crosslinker is important in determining the nature of the final membrane. If, for example, an inadequate amount of crosslinker or an extremely large excess of crosslinker is used, crosslinking will be insufficient and the membrane thus weak. If, on the other hand, an excessive amount of crosslinker is used, crosslinking will be excessive and the membrane thus brittle and/or impervious to analyte diffusion. Thus, there is an optimal ratio of a given polymer to a given crosslinker that should be used to prepare a desirable or useful membrane. By way of example, the optimal polymer to crosslinker ratio by weight is typically from about 4:1 to about 32:1 for a polymer of any of Formulas 3-6 above and a poly(ethylene glycol) diglycidyl ether crosslinker, having a molecular weight of about 200 to about 400. Most preferably, this range is from about 8:1 to about 16:1. Further by way of example, the optimal polymer to crosslinker ratio by weight is typically about 16:1 for a polymer of Formula 4 above, wherein $[n/(n+l+p)] \times 100\% \approx 10\%$, $[l/(n+l+p)] \times 100\% \approx 80\%$, and $[p/(n+l+p)] \times 100\% \approx 10\%$, or for a polymer of Formula 5 above, wherein $[n/(n+m+l+p)] \times 100\% \approx 10\%$, $[m/(n+m+l+p)] \times 100\% \approx 10\%$, $[l/(n+m+l+p)] \times 100\% \approx 70\%$, $[p/(n+m+l+p)] \times 100\% \approx 10\%$, and $r \approx 110$, and a poly(ethylene glycol) diglycidyl ether crosslinker having a molecular weight of about 200.

The membrane solution can be coated over a variety of biosensors that may benefit from having a membrane disposed over the enzyme-containing sensing layer. Examples of such biosensors include glucose sensors and lactate sensors. (See U.S. Pat. No. 6,134,461 to Say et al., filed on Mar. 4, 1998.) The coating process may comprise one or more of a variety of techniques, such as spin-coating, dip-coating, or dispensing droplets of the membrane solution over the sensing layers, and the like, followed by curing under ambient conditions typically for one to two days. The particular details of the coating process (such as dip duration, dip frequency, number of dips, or the like) may vary depending on the nature (i.e., viscosity, concentration, composition, or the like) of the polymer, the crosslinker, the membrane solution, the solvent, and the buffer, for example. Further, the composition of the coating material can vary from dip to dip. For example, the polymer composition itself could vary. As another example, as will be described below, a superoxide-dismutase/catalase catalyst or a superoxide-dismutase/catalase mimic can be incorporated into the polymeric dipping material, and in such a case, the concentration of the catalyst or mimic could vary in the successive dippings, or it could be completely absent in some of the dippings. Conventional equipment may be used for the coating process, such as a DSG D1L-160 dip-coating or casting system of NIMA Technology in the United Kingdom.

Example of Sensor Fabrication

Sensor fabrication typically consists of depositing an enzyme-containing sensing layer laid over a working electrode, and casting the diffusion-limiting membrane layer over the sensing layer, as well as (optionally and preferably) over the counter and reference electrodes. The procedure below concerns the fabrication of a two-electrode sensor, such as that depicted in FIGS. 2A-2C. Sensors having other configurations such as a three-electrode design can be prepared using similar methods.

A particular example of sensor fabrication, wherein all numerical designations are approximate, is now provided. A sensing layer solution was prepared from a 7.5 mM HEPES solution (0.5 µL, pH 8), containing 1.7 µg of the polymeric osmium mediator compound L, as disclosed in the Published Patent Cooperation Treaty (PCT) Application, International Publication No. WO 01/36660 A2 of Mao et al., filed on Nov. 14, 2000; 2.1 µg of glucose oxidase (Toyobo); and 13 µg of poly(ethylene glycol) diglycidyl ether (molecular weight 400). Compound L is shown below.

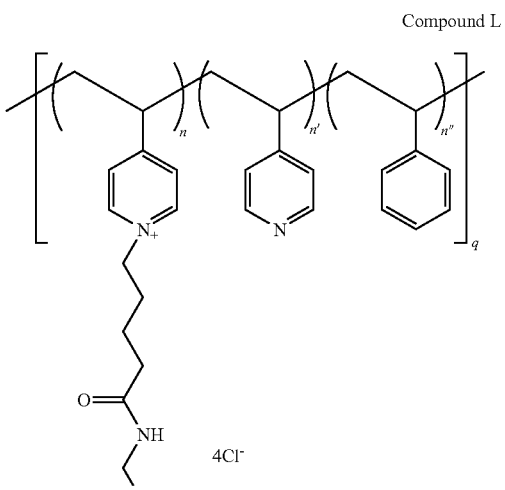

Compound L

-continued

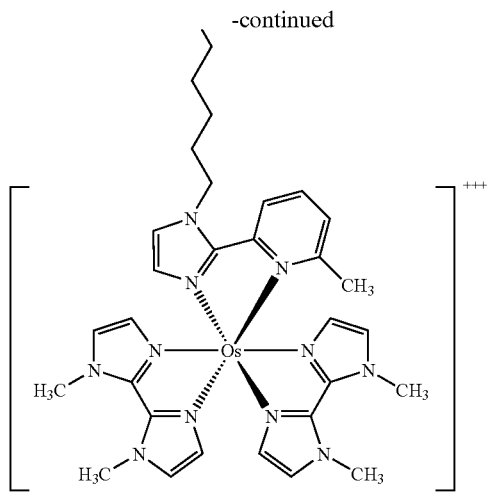

The sensing layer solution was deposited over carbon-ink working electrodes and cured at room temperature for two days to produce a number of sensors. A membrane solution was prepared by mixing 4 volumes of a polymer of Formula 4 above, dissolved at 64 mg/mL in 80% EtOH/20% HEPES buffer (10 mM, pH 8), and one volume of poly(ethylene glycol) diglycidyl ether (molecular weight 200), dissolved at 4 mg/mL in 80% EtOH/20% HEPES buffer (10 mM, pH 8). The above-described sensors were dipped three times into the membrane solution: about 5 seconds per dipping, with intervals of about 10 minutes between dips. The sensors were then cured at room temperature and normal humidity for 24 hours.

An approximate chemical structure of a section of a typical membrane prepared according to the present invention is shown in FIG. 1. Such a membrane may be employed in a variety of sensors, such as the two- or three-electrode sensors described previously herein. By way of example, the membrane may be used in a two-electrode amperometric glucose sensor, as shown in FIGS. 2A-2C (collectively FIG. 2) and described below.

The amperometric glucose sensor 10 of FIG. 2 comprises a substrate 12 disposed between a working electrode 14 that is typically carbon-based, and an Ag/AgCl counter/reference electrode 16. A sensor or sensing layer 18 is disposed on the working electrode. A membrane or membrane layer 20 encapsulates the entire glucose sensor 10, including the Ag/AgCl counter/reference electrode.

The sensing layer 18 of the glucose sensor 10 consists of crosslinked glucose oxidase and a low potential polymeric osmium complex mediator, as disclosed in the above-mentioned Published PCT Application, International Publication No. WO 01/36660 A2. The enzyme- and mediator-containing formulation that can be used in the sensing layer, and methods for applying them to an electrode system, are known in the art, for example, from the above-mentioned U.S. Pat. No. 6,134,461 of Say et al. According to the present invention, the membrane overcoat was formed by thrice dipping the sensor into a membrane solution comprising 4 mg/mL poly(ethylene glycol) diglycidyl ether (molecular weight of about 200) and 64 mg/mL of a polymer of Formula 4 above, wherein $[n/(n+l+p)] \times 100\% \approx 10\%$; $[l/(n+l+p)] \times 100\% \approx 80\%$; and $[p/(n+l+p)] \times 100\% \approx 10\%$, and curing the thrice-dipped sensor at ambient temperature and normal humidity for at least 24 hours, such as for about one to about two days. The q value for such a membrane overcoat may be greater than or equal to about 950, where n is 1, l is 8, and p is 1.

Provision of Bioactive Agents or Catalysts Relative to a Membrane of an Analyte Sensor As mentioned previously, the functioning and performance of a transcutaneous analyte sensor may be complicated by an immune system response to the insertion of the transcutaneous portion of the sensor. Broadly speaking, it is possible to intervene in such an immune system response in a variety of ways, such as by providing at least one bioactive agent or biological response modifier, such as a drug, a steroid, a protein hormone, an antibody, a cytokine, or any suitable combination thereof, that has an effect on cells of the immune system, at an insertion, sensor, or implant site. (See, for example, U.S. Pat. No. 6,497,729 B1, filed on Nov. 19, 1999, and U.S. Patent Application Publication No. 2003/0099682 A1, filed on Jan. 31, 2002, each of Moussy et al., and U.S. Patent Application Publication Nos. 2003/0199837 A1 of Vachon, filed on Apr. 22, 2002, and 2003/0031699 A1 of Van Antwerp, filed on Sep. 30, 2002.) It is also possible to provide an agent that can affect the concentration of a metabolite in the extracellular fluid surrounding such a site and thereby mediate the immune response and its effect. For example, it is theorized that certain metals such as titanium, zirconium, palladium, gold, and platinum, or certain inorganic metal oxides, such as titanium dioxide and zirconium oxide, may inhibit the production of reactive oxygen species that are associated with inflammation at an implant site. (See, for example, Published PCT Application, International Publication No. WO 03/063925 A1 of Bjursten et al., filed on Jan. 31, 2003.). Further by way of example, when the metabolite comprises oxygen free radicals, either non-catalytic, antioxidant scavengers or superoxide-dismutase/catalase catalysts may be provided to reduce the concentration of the oxygen free radicals and thereby mediate the immune response. Antioxidant scavengers neutralize oxygen species by taking part in reactions that consume the oxygen species and the scavenger. Superoxide-dismutase/catalase catalysts, on the other hand, metabolically inactivate reactive oxygen species, while remaining unchanged by the reaction and thus available for further catalytic activity.

As mentioned above, catalase is a superoxide-dismutase/catalase catalyst that catalyzes the decomposition of hydrogen peroxide. More broadly, agents that catalyze the decomposition of hydrogen peroxide make up a large class and come from a variety of sources, such as microbial, plant, and animal cells. For example, according to the International Union of Biochemistry, there is a large group of oxidoreductase enzymes that includes a subgroup (EC 1.11) of peroxidases that act on hydrogen peroxide as electron acceptors. These peroxidases generate water and an activated donor molecule when acting on hydrogen peroxide. Catalase (hydrogen peroxide oxidoreducase, EC 1.11.1.6) is but one of these peroxidases that more specifically generates water and oxygen when acting on hydrogen peroxide. Further, some peroxidases (sometimes referred to as catalase-peroxidase) from various microorganisms, such as *Penicillium simplicissimum*, exhibit both peroxide and catalase activity. Superoxide-dismutase/catalase catalysts encompass any of the foregoing peroxidases, and any non-proteinaceous mimic thereof. According to the present invention, these superoxide dismutase/catalase catalysts act to deplete concentrations of the metabolite, hydrogen peroxide, in useful ways, such as in biosensor applications, as further described herein.

Yet further catalytic agents that act on local concentrations of one or more metabolite(s) may be usefully employed according to the present invention. Merely by way of example, catalysts that act to decompose the metabolite, peroxynitrite, may be so employed. (See, for example, U.S. Pat.

No. 6,245,758 of Stern et al., filed on Sep. 9, 1996, and U.S. Pat. No. 6,448,239 of Groves et al., filed on Jun. 1, 2000; U.S. Patent Application Publication No. U.S. 2003/0055032 A1 of Groves et al., filed on Jul. 29, 2002; and Published PCT Applications, International Publication Nos. WO 95/31197 A1 of Stern et al., filed on May 9, 1995, WO 98/43637 A1 of Riley et al., filed on Mar. 26, 1998, and WO 00/75144 A2 of Groves et al., filed on Jun. 2, 2000.) Such catalysts include metalloporphyrin peroxynitrite catalysts, for example. (See, for example, Szabo et al., Part I: Pathogenetic role of peroxynitrite in the development of diabetes and diabetic vascular complications: studies with FP15, a novel potent peroxynitrite decomposition catalyst, Mol. Med. 2002, 8(10), 571-580; Mabley et al., Part II: Beneficial effects of the peroxynitrite decomposition catalyst FP15 in murine models of arthritis and colitis, Mol. Med. 2002, 8(10), 581-590; and Pacher et al., Potent metalloporphyrin peroxinitrite decomposition catalyst protects against the development of doxorubicin-induced cardiac dysfunction, Circulation, Feb. 18, 2003; 107(6), 896-904.)

Thus, according to an embodiment of the present invention, at least one catalyst is provided in proximity to a sensor and within a sufficient distance from the sensor such that the catalyst changes the concentration of at least one metabolite in the extracellular fluid environment surrounding and in contact with the sensor. The provision of such a catalyst in this manner may be used to influence various metabolite families and associated pathways, such as oxygen radicals, superoxide, hydrogen peroxide, and any associated oxidant or metabolic pathway; nitric acid, peroxynitrite, and any associated nitric acid or metabolic pathway; nitric oxide, nitric chloride, and any associated metabolic pathway; and any catabolic pathway of intermediary metabolism. The provision of superoxide-dismutase/catalase catalysts is further described herein by way of example.

Incorporation of Compounds with Superoxide Dismutase and/or Catalase Activity into the Outer Membrane of a Glucose Sensor Polymers of the present invention have a large number of heterocyclic nitrogen groups, such as pyridine groups, only a few percent of which are used in crosslinking during membrane formation. The membrane thus has an excess of these groups present both within the membrane matrix and on the membrane surface. More specifically, incorporation of superoxide-dismutase/catalase catalysts, such as an enzyme or an enzyme mimic, is accomplished by using the glucose biosensor membrane chemistry, which relies on crosslinks formed between glycidyl ethers (supplied by the crosslinker triglycidyl glycerol) and either amino groups (from enzymes, such as glucose oxidase) or pyridyl groups (from the poly(vinylpyridine)-based membrane polymer). Since SOD contains amino groups and SOD mimics can be prepared that contain amino or pyridyl groups, the SOD enzyme or mimic thereof can be incorporated throughout the bulk of the membrane material. This bulk loading stands in contrast to the membrane surface decoration procedure, as described by Udipi, Ornberg, Riley, and colleagues (above-mentioned U.S. Pat. No. 6,525,041; above-mentioned Published PCT Application, International Publication No. WO 00/72893 A2; and J. Biomed. Mater. Res. 2000; 51(4): 549-560). In the foregoing journal publication, the authors state that they achieve a maximum of about 1 weight percent of SOD mimic relative to the membrane (sometimes referred to herein as "weight percent loading," or "weight %"), while in the foregoing Published PCT application, a weight percent loading of up to 3% is described.

The bulk loading procedure of the present invention, described herein, in contrast, can readily yield membranes with at least about a 10 weight percent loading of an SOD mimic, and possibly higher levels also achievable. A higher loading efficiency offers the potential for greater anti-inflammatory activity, greater robustness and/or an increased shelf life. Superoxide-dismutase/catalase catalysts can be incorporated into a glucose-flux-reducing membrane in a variety of ways, some of which can result in the catalyst being irreversibly bound to the membrane, by covalent bonds. Weaker types of chemical association between the polymers and the catalyst include ion-exchange interactions. Finally, functionality of the superoxide-dismutase/catalase catalysts could be supported as well by highly constraining polymer structures that effect a containment or adsorption of the catalyst, and allow it to leach out over the lifetime of the sensor.

The appropriate weight percent level of the SOD catalyst or mimic may be determined by empirical observation of the performance and the effectiveness of membrane-covered sensors in human subjects. For example, as described below in relation to Example 3, sensors covered with membranes having a weight loading of about 5% of a mimic (MnTPyP) showed a lower incidence of, or complete absence of, low-glucose-reading incidents, such that this weight loading of mimic was considered appropriate for these sensors. The effective weight percent loading may vary with the effectiveness of the catalyst. In separate assays, the catalytic effectiveness ($k_{cat}$) of various superoxide dismutase mimics has been shown to vary over several orders of magnitude (see FIG. 1 of Batinic-Haberle, Manganese porphyrins and related compounds as mimics of superoxide dismutase, Methods Enzymol. 2002, 349, 223-33). Further, the effective weight percent loading may vary somewhat as a function of the relative weights of the specific mimic(s) and specific polymer(s) that are used as membrane components. Lower limits of weight % loading are contemplated herein, as may be evident from empirical measures of sensor performance and/or the defining of a useful threshold level of performance, such as performance in human subjects, particularly upon the accumulation of a sufficient amount of data. Upper limits of weight % loading are also contemplated herein, and may be founded on constraints in the synthetic process and/or on evidence of negative consequences of an excess amount of mimic on the physical characteristics or the performance of the membrane. These considerations notwithstanding, it is contemplated that the weight percent of a MnTPyP mimic relative to the membrane is preferably from about 0.0001 to about 30 weight %, more preferably from about 0.001 to about 20 weight %, and most preferably from about 0.01 to about 10 weight %. Further, it is contemplated that these weight percent ranges are applicable to other catalysts and mimics, particularly when such amounts are expressed in terms of comparable weight relative to a sensor, or comparable weight relative to a sensing surface area, as described below.

As described above, some embodiments of the present invention include a superoxide-dismutase/catalase catalyst that is not covalently incorporated into a polymeric membrane, but is otherwise associated with a polymeric membrane. By way of example, a superoxide-dismutase/catalase catalyst or mimic may be held within the membrane by ionic interactions. In such cases, the catalyst or mimic may be allowed to leach out from the polymer. In other embodiments, the catalyst or mimic can be adsorbed onto the membrane, or held within it by the polymeric matrix. In still other embodiments (see "Embodiments in which the catalyst is disposed in proximity to the sensor," below), the superoxide-dismutase/catalase catalyst or mimic may not be strictly associated with a polymeric membrane covering a sensor surface per se, but rather may be disposed in proximity with respect to a polymeric membrane that is sufficient to have a beneficial effect on membrane or sensor performance. In these various embodiments, it may be more appropriate to express the amount of catalyst or mimic present in terms other than weight % relative to the membrane, such as weight relative to the sensing surface area of the sensor. For example, as described in Example 2 and Example 3 below, a mimic in an amount of about 5 weight % relative to a membrane has a clear beneficial effect on sensor performance. For a sensor having a sensing surface area of about 7 $mm^2$, this value may be expressed as a total mimic amount of about 20 micrograms/sensor, or about 3 micrograms/$mm^2$ of the sensing surface area. Such a value may be used as an initial benchmark for estimating an effective amount of a superoxide-dismutase/catalase catalyst or mimic when such is disposed within the locale of the sensor, but not necessarily on the flux-limiting membrane per se, as is the case in some embodiments described below.

According to the present invention, a catalyst or mimic, such as a superoxide-dismutase/catalase mimic, may be associated with a polymeric matrix of a sensor. For example, a catalyst or a mimic may be closely held in association with a flux-limiting membrane of a sensor by way of covalent bonds, as previously described. As metabolites diffuse in the extracellular fluid environment surrounding a sensor, even a closely-held catalyst or mimic that affects the local concentration of metabolites, such as superoxide and hydrogen peroxide, affects not only the environment in immediate contact with the sensor, but also a more extended environment that surrounds the sensor. Thus, according to the present invention, the catalyst or mimic need not be associated or closely associated with a flux-limiting membrane per se, but need only be sufficiently local relative to the sensor to affect the concentration of one or more metabolite(s), such as superoxide and/or hydrogen peroxide, in the environment surrounding the sensor. Thus, in some embodiments of the invention, a catalyst or a mimic is not associated with a flux-limiting membrane, per se, but is instead associated with any membrane, surface or reservoir that is present in a location sufficiently near the sensing surface, such that metabolite concentration is affected by the presence of the catalyst or mimic. For example, according to an embodiment of the invention, a catalyst or mimic may be disposed on an inner surface of a protective covering of a transcutaneous sensor.

Superoxide-dismutase/catalase catalysts or mimics may be incorporated into the existing membrane formulation in various ways. For example, a preparation of one or more enzyme(s), such as superoxide dismutase and/or catalase, may be incorporated into a membrane covering a sensing surface, or into a matrix or matrices, or a reservoir or reservoirs, in a vicinity or locale of the sensing surface. Such enzymes can be derived from various natural sources (including plant, animal, bacteria, or yeast), or through genetic engineering and production of improved versions of the proteins by known methods. These enzymes may contain suitable metal elements or transition metal elements, such as manganese, iron, copper, zinc, or any combination thereof, merely by way of example. For example, superoxide dismutase may comprise a metal such as manganese, iron, copper, or zinc; catalase may comprise iron, and thus, be referred to as a "heme" enzyme; and a superoxide-dismutase/catalase catalyst may comprise any suitable metal.

According to embodiments of the invention, one or more compound(s) from a broad class of non-proteinaceous compounds that mimic the catalytic action of superoxide dismutase and/or catalase may be used in place of, or in addition to, superoxide dismutase and/or catalase. Examples of such compounds, include, but are not limited to the following: (1) manganese 5,10,15,20-tetra(4-pyridyl)-21H,23H-porphine chloride (hereafter MnTPyP); (2) MnTPyP quaternized at one to three of the pyridyl sites; (3) MnTPyP quaternized at all four pyridyl sites; (4) MnTPyP quaternized at least one pyridyl site by a quaternizing moiety and having a free pyridyl or an amino functional group attached to at least one quaternizing moiety; (5) a compound comprising manganese coordinated in a macrocyclic, penta-amine ring, and also comprising a reactive amino or pyridyl moiety, such as M40403 or M40470, from Metaphore Pharmaceuticals, Inc. (St. Louis, Mo.); (6) a compound, other than that of item (5) above, having SOD activity, such as any such compound described by Metaphore Pharmaceuticals, Inc. or in the above-mentioned Published PCT Application, International Publication No. WO 00/72983 A2, or in U.S. Pat. No. 5,696,109 to Malfroy-Camine et al., filed on Jun. 7, 1995, such as a transition metal chelate of pentaaza-cyclopentadecane compound or a salen compound (for example, a manganese or an iron chelate of any such compound), derivatized with a reactive amino or pyridyl group; (7) a bipyridine manganese complex or a cyclic salen-transition-metal complex, such as any disclosed by Eukarion, Inc. (Bedford, Mass.) or in above-referenced U.S. Pat. Nos. 6,403,788, 6,541,490, 6,573,257 and 6,589,948; (8) any suitable manganese porphyrin, iron porphyrin, manganese polyamine, iron polyamine, manganese salen, and iron salen complex, such as those described by Batinic-Haberle (Manganese porphyrins and related compounds as mimics of superoxide dismutase, Methods Enzymol. 2002, 349, 223-33), and in published patents or patent applications (U.S. Pat. No. 5,227,405 of Fridovich et al., filed on Sep. 28, 1988, U.S. Pat. No. 5,994,339 of Crapo et al., filed on Jun. 7, 1995, U.S. Pat. No. 6,103,714 of Fridovich et al., filed on Jul. 24, 1996, U.S. Pat. No. 6,127,356 of Crapo et al., filed on Jun. 7, 1996, U.S. Pat. No. 6,479,477 of Crapo et al., filed on Apr. 23, 1999, and U.S. Pat. No. 6,544,975 of Crapo et al., filed on Jan. 25, 2000, and U.S. Patent Application Publication Nos. 2002/0082490 A1 of Roeper et al., filed on Jul. 20, 2001, and 2003/0069281 A1 of Fridovich et al., filed on Jun. 14, 2001); (9) any of the biporphyrin superoxide-dismutase/catalase mimics of Bruice (above-mentioned U.S. Pat. Nos. 5,202,317 and 5,217,966); and (10) the compound manganese (III) tetrakis (4-benzoic acid) porphyrin (hereafter MnTBAP), marketed by Alexis Biochemicals (Paris, France), whose use as a superoxide dismutase mimic is described by Weill et al., in the above-mentioned U.S. Patent Application Publication No. U.S. 2003/0118577 A1.

SENSOR PERFORMANCE EXAMPLES

Sensor Performance Example 1

Performance of Sensors With and Without Diffusion-Limiting Membranes

The performance of sensors with diffusion-limiting membranes was compared to that of naked or membrane-less sensors in terms of the current output in response to varying concentrations of glucose. Glucose concentration ranged from zero to a high of 30 mM, the upper portion of the range being consistent with the pathophysiology of uncontrolled diabetic hyperglycemia.

A calibration experiment was conducted in which fifteen sensors lacking membranes (Control Group, Set 1) were tested simultaneously, and separately, eight sensors having diffusion-limiting membranes according to the present invention (Test Group, Set 2) were tested simultaneously. The purpose of this particular experiment was focused on quantifying the effect on sensor performance of regulating the glucose diffusion rate, and thus the test membranes were conventional in that they did not include superoxide-dismutase/catalase catalysts.

The testing protocol, briefly stated, was to measure the current elicited from the sensor as a function of exposure to sample glucose concentrations up to 30 mM, all testing at 37° C. In the Test Group (Set 2) the membranes were prepared from polymers of Formula 4, above, and poly(ethylene glycol) diglycidyl ether (PEGDGE) crosslinkers, having a molecular weight of about 200. In the calibration experiment for each of Set 1 and Set 2, the sensors were placed in a phosphate buffered saline solution (pH 7) and the output current of each of the sensors was measured as the glucose concentration was increased. The measured output currents ($\mu A$ for Set 1; nA for Set 2) were then averaged for each of Set 1 and Set 2 and plotted against glucose concentration (mM) (FIG. 3).

As shown in FIG. 3, the calibration curve for the control sensors (Set 1, lacking membranes) is approximately linear over a very small range of glucose concentrations, from zero to about 3 mM, or 5 mM at most. This result indicates that the membrane-free sensors are relatively insensitive to variations in glucose concentration above 10 mM, a level well below the upper half of the clinically relevant range of glucose concentration, which extends up to about 30 mM. By contrast, the calibration curve for the test sensors (Set 2, those having diffusion-limiting membranes) is substantially linear over the full range of clinically relevant glucose concentrations, from zero to about 30 mM, as demonstrated by the best-fit line ($y=1.2502x+1.1951$; $R^2 \approx 0.997$) as shown in FIG. 3.

In FIG. 3, the y-axis for the membrane-less sensors is on the right hand side of the graph, the scale shown in $\mu Amps$ ($\mu A$); while the y-axis for the membrane-covered sensors is on the left hand side of the graph, in nanoAmps (nA). At a 30 mM glucose concentration, the membrane-less sensor responds with a signal of about 1.8 $\mu A$, while the membrane-covered sensor delivers about 45 nA. In absolute terms, the response of the membrane-covered sensor is approximately 2% of the magnitude of the membrane-less sensor, but the advantage yielded by the performance curve as a whole is that it is linear. Linearity of this type creates a greater degree of confidence in the accuracy of sensor readings, as the change in the signal in proportion to the change in analyte (in this case, glucose) concentration is the same throughout the analyte concentration range of interest.

Sensor Performance Example 2

Performance of Sensors with Catalyst-Enhanced Membranes in Vitro Tests

A catalytic membrane solution that included a buffer solution and a membrane polymer preparation was prepared. The buffer solution comprised 4 parts of ethanol to 1 part of 10 mM HEPES, for a final concentration of 0.02 mM HEPES. The membrane polymer preparation comprised 116 mg/ml of a formulation called 10Q5, as depicted below in Formula 7 (wherein x=0.85, y=0.1, z=0.05, n=9, m=1, and p=about 10), 8 mg/ml triglycidyl glycerol (the crosslinker), and 7.5 mg/ml manganese 5,10,15,20-tetra(4-pyridyl)-21H,23H-porphine chloride (MnTPyP), a compound possessing both superoxide dismutase and catalase activity.

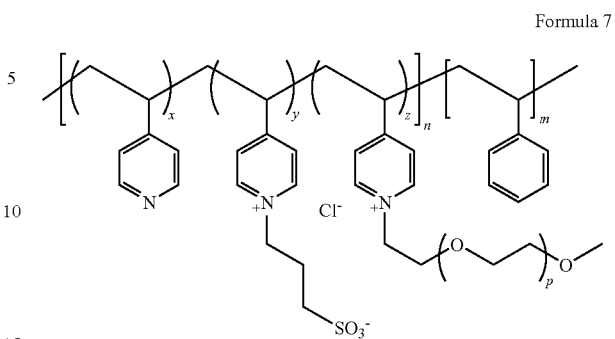

Formula 7

A batch of sensors was prepared by dipping membrane-less sensors (which contained previously deposited, wired-enzyme sensing layers) three times, in succession, into the catalytic membrane solution. Each resulting sensor membrane contained approximately 13 micrograms of the catalyst, MnTPyP, or a load with respect to the membrane of about 5.7 weight %. Incorporation of the catalyst was broadly verified by the visual observation of an intense dark color imparted to the membrane.

FIG. 4 depicts the in vitro performance of a group of individual sensors in terms of the current output in nanoAmps (nA) as a function of the glucose concentration (from 0 to 30 mM) to which the sensors were exposed in a bench-top experiment. Two features of the graphed results are of interest. First, the graph is substantially identical to the results observed for a simultaneously prepared group of control sensors (with conventional membranes, containing no MnTPyP), with regard to the sensitivity and coefficient of variation (of the individual slopes) within the group. Second, the slopes of the curves are very close to those shown in FIG. 3 for the membrane-covered sensors. For example, in both FIG. 3 and FIG. 4, a concentration of 30 mM glucose elicits a current output of approximately 30 nA. These data, collectively, taken from tests run with separate preparations, and at different times, offer strong support for the robustness of the method of preparing membrane-covered sensors, for the consistency of performance, and for the absence of any negative effects of an incorporated superoxide-dismutase/catalase mimic on the linearity of sensor performance in this bench-top context.

Sensor Performance Example 3

Comparison of Performance of Sensors with a Conventional Membrane and Sensors with a Catalyst-Enhanced Membrane in Human Subjects The performance of sensors with catalyst-enhanced membranes was tested in 14 volunteer, non-diabetic human subjects, and compared to the simultaneous performance of sensors with conventional membranes that have no catalyst enhancement. The human-subject study was approved by the TheraSense Institutional Review Board of TheraSense, Inc. of Alameda, Calif. Subjects were informed of risks and consented to participate in view of possible risks, such as bruising, edema, erythema, and excessive bleeding. Subjects were free to discontinue the study at any time, and were limited to three sensor-attachment attempts over the course of the three-day study. Following the study and sensor removal, subjects were examined for any manifestation of the identified risks.

In this experiment, each of the volunteers was fitted simultaneously with two transcutaneous glucose sensors, a control sensor and an experimental sensor. The control sensor and the experimental sensor were prototypes of a Navigator™ continuous glucose-monitoring system manufactured by TheraSense, Inc. Each of the sensors had a protective membrane as described previously, but the membrane of the control sensor was not catalytically enhanced, while the experimental sensor was enhanced with a MnTPyP catalyst in an amount of about 5% by weight with respect to the weight of the polymer membrane. Each of the sensors transmitted its data wirelessly, by radio frequency transmission to an external handheld display unit that stored and processed the data.

For each human subject, glucose values were automatically and continuously collected from the control sensor and the experimental sensor over a three-day period to obtain a stream of control sensor data and a stream of experimental sensor data, respectively. Additionally, each human subject manually collected glucose values from his or her capillary blood using a Freestyle™ glucose strip-reading meter manufactured by Therasense, Inc. at irregular intervals, but at a rate of about 10 to about 15 samples per day. The human-subject data and associated statistical data, shown in Table 2 below, were then compared to evaluate the effect of the superoxide-dismutase/catalase catalyst associated with the experimental sensor.

TABLE 2

Comparison of Performance for Control and Experimental Sensors

| Sensor Type | Control (Not Enhanced) | Experimental (Catalyst Enhanced) | Comment |
| --- | --- | --- | --- |
| Number of Subjects | 14 | 14 | Identical, by design |
| Number of Data Points | 644 | 681 | Comparable, by design |
| Clarke Statistics | | | |
| % A (accurate zone) | 77.2% | 84.0% | 8.8% improvement |
| % B (inaccurate zone) | 22.5% | 15.7% | 28% improvement |
| % D (indifferent zone) | 0.3% | 0.3% | no change |
| Average Error | 13.0% | 10.7% | 18% improvement |
| Noise Parameter | 0.050 | 0.037 | 26% improvement |

In a first comparison, the accuracy of data from the control sensors (control sensor data) and data from the experimental sensors (experimental sensor data), relative to the reference data from coincidentally obtained, manual capillary blood measurements, were compared. This involved analyzing the control sensor data and the experimental sensor data using Clarke statistics to characterize the error relative to the reference data and to determine an average error for each of the two data streams.

In the characterization and determination of error associated with the experimental sensors, the percentage of the data associated with the accurate zone was about 84.0%; the percentage of the data associated with the inaccurate zone and indifferent zone was about 15.7% and about 0.3%, respectively; and the overall error was about 10.7%. These values compare favorably with those associated with the control sensor (see Table 2). More particularly, the accuracy of experimental sensors was about 8.8% higher than that of the control sensors; the inaccuracy of the experimental sensors was about 28% less than that of the control sensors; and the overall average error of the experimental sensors was about 18% less than that of the control sensors. These data demonstrate that the experimental sensors are capable of providing data of greater accuracy than the data provided by the control sensors.

In a second comparison, data from the control sensors and the experimental sensors with respect to noise within the data stream were compared. This involved calculating a "noise parameter" for the control sensors and a noise parameter for the experimental sensors to compare the level of noise associated with each of the two data streams. Each noise parameter was calculated by determining the percentage difference between (a) the average rate of change in glucose concentration (in mg/dL per minute) for a complete stream of continuous data from each sensor and (b) the average rate of change of glucose concentration (in mg/dL per minute) for the same data stream, after it has been smoothed by the application of a 10-minute boxcar filter. As data-smoothing inherently reduces the mean rate of change, the value associated with the latter, smoothed average rate (b, above) is at least some degree less than the value for the former, raw average rate (a, above). If the raw data are relatively smooth to begin with, these two average rates will be very similar, such that the noise parameter will be relatively small. If the raw data are noisy, the two average rates will differ more greatly, such that the noise parameter will be relatively large. Thus, the noise parameter is relatively small for smooth data and relatively large for noisy data.

In this noise comparison, the noise parameter associated with the experimental sensors was about 0.037, while that associated with the control sensors was about 0.050, as shown in Table 2. The experimental sensors thus outperformed the control sensors by reducing noise by about 26%. These data demonstrate that experimental sensors are capable of providing glucose readings with much less noise than are control sensors.

The foregoing comparisons demonstrate that a superoxide-dismutase/catalase catalyst can be used according to the present invention to enhance or improve sensor performance.

In the course of this experiment, the experimental sensors and the control sensors were also evaluated as to the occurrence or non-occurrence of low-glucose-reading incidents. In this evaluation, it was determined that no low-glucose-reading incidents occurred when catalyst-enhanced, experimental sensors were used. By contrast, it was determined that several low-glucose-reading incidents occurred when non-enhanced, control sensors were used. One such incident is described below in relation to FIG. 5, after the following general discussion of such incidents.

When a transcutaneous sensor is used by either a diabetic or a non-diabetic subject, it may provide, on occasion, a glucose reading that an experienced observer would consider spurious, as not being reflective of the subject's systemic glucose level. These low-glucose-reading incidents generally occur in the first 24 hours following transcutaneous placement of the sensor, especially when the subject is sleeping. A non-diabetic human subject is an appropriate model for the study of these incidents, as even though diabetic and non-diabetic human subjects have different glucose values in absolute terms, they show broadly similar glucose profiles as to low-glucose-reading incidents. A low-glucose-reading incident may be recognized in a healthy, non-diabetic human when a glucose reading is below about 60 mg/dL, as such a person rarely has a blood glucose value that is actually that low. Such an incident may also be recognized when the person's physical movement causes the glucose reading to quickly return to a normal level. A low-glucose-reading incident might also be recognized by comparing the glucose reading from the transcutaneous sensor with a glucose reading obtained simultaneously from a conventional blood sample, and noting a significant discrepancy. This latter comparison method is generally impractical in an experiment of the design described herein, as these low-glucose-reading incidents generally occur when a person is sleeping and thus not able to obtain a conventional blood sample (i.e., a capillary blood sample obtained via a blood-lancing device), manipulate the sample (i.e., apply it to a conventional test-strip), and obtain a reading from a glucose meter (i.e., a conventional glucose meter that is used in connection with a conventional test-strip).

By any of the means described above, experienced or informed observers may recognize low-glucose-reading incidents as being spurious. Even so, these incidents remain highly problematic, as falsely indicating hypoglycemia. Further, if such an incident occurs soon after the sensor is inserted, calibration of the sensor may be compromised such that the problem is amplified. The problem of low-glucose-reading incidents appears to result from variations in human subjects rather than from quality variations in transcutaneous sensors. That is, data from a known group of human subjects suggests that these incidents occur more often with some subjects than with others. Thus, it appears that these incidents might be better understood in terms of the variability of the biology and biochemistry of the subcutaneous space in human subjects, as well as other subjects. In this regard, it is contemplated that the presence of cells, such as neutrophils, from the immune system, and/or the metabolic activity of those cells, such as the consumption of glucose and the generation of highly reactive oxidative species, such as superoxide ion and hydrogen peroxide, may play a role in these incidents.

In this evaluation of low-glucose-reading incidents, experimental data obtained from one non-diabetic human subject in the manner described above was charted over a three-day period, as shown in FIG. 5. These data included the continuous readings of glucose concentration (mg/dL) from the control sensor, as represented by the darkly shaded "curve;" the continuous readings of glucose concentration (mg/dL) from the experimental sensor, as represented by the lightly shaded "curve;" and the intermittent glucose readings that were manually obtained from capillary blood, as represented by shaded triangles. It should be noted that, for reasons mentioned above, capillary blood reference data were not obtained during typical periods of sleep. As low-glucose-reading incidents typically occur during sleep, the capillary reference data, while shown for certain times, were not relevant to this evaluation.

A portion of the curve associated with the control sensor (i.e., the sensor having a membrane, but no catalyst enhancement) is circled in FIG. 5 to highlight a particular low-glucose-reading incident. This incident appears to be typical of those associated with conventional sensors in that it occurred within the first 24 hours of its transcutaneous use; it occurred from late in the night to early in the morning, a typical sleep period; and it was associated with apparent glucose concentrations that are below 60 mg/dL and fell as low as about 22 mg/dL. If true, a glucose concentration as low as 22 mg/dL would indicate a threateningly dangerous level of hypoglycemia. In contrast, a corresponding portion of the curve associated with the experimental sensor (i.e., the sensor having a membrane, as well as MnTPyP enhancement) that lies directly above the circle in FIG. 5, shows no such low-glucose-reading incident. That is, this portion of the curve corresponds to normal glucose readings from about 65 mg/dL to about 85 mg/dL that were obtained from the same person during the same period. The data from this experiment support the conclusion that during the period associated with the low-glucose-reading incident, the control sensor data were false and the experimental sensor data were accurate with respect to systemic blood glucose levels.

The foregoing results demonstrate that under conditions in which a conventional sensor produces a low-glucose-reading incident, a catalyst-enhanced experimental sensor according to the present invention produces no such incident. These results suggest that the catalyst acts to reduce, mitigate, or prevent low-glucose-reading incidents. It is believed, without being so bound, that the catalyst reduces the local concentration of metabolites, such as superoxide and hydrogen peroxide, in the area surrounding the sensor, and thereby enhances the performance of the transcutaneous sensor.

The results of the experiment described above demonstrate that relative to a non-enhanced sensor, a catalyst-enhanced sensor according to the present invention provides data of higher accuracy and less noise. The results further demonstrate that a catalyst-enhanced sensor according to the present invention can operate without the occurrence of low-glucose-reading incidents that are associated with non-enhanced sensor.

Embodiments in which a Catalyst is Disposed in Proximity to the Sensor

According to an embodiment of the invention, a superoxide-dismutase/catalase catalyst or mimic may be incorporated into a microdialysis membrane and thus into an analyte sensor, such as a glucose sensor, that employs such a microdialysis membrane. Examples of suitable microdialysis membranes, such as those suitable for glucose sensing, include those developed by companies such as Hoffman-La Roche (Basel, Switzerland) and Menarini Diagnostics (Florence, Italy), and those disclosed in various patents and patent applications, such as U.S. Pat. No. 5,640,954 of Pfeiffer et al., filed on May 5, 1995, U.S. Pat. No. 6,091,976 of Pfeiffer et al., filed on Oct. 28, 1998, and U.S. Pat. No. 6,591,126 of Reoper et al., filed on Jul. 20, 2001; U.S. Patent Application Publication Nos. 2001/0041830 A1 of Varalli et al., filed on May 7, 2001, and 2002/0042407 A1 of Fridovich et al., filed on Jun. 14, 2001; and European Patent Application No. EP 1153571 A1 of Varalli et al., filed on May 3, 2001. In such a glucose-sensing system, for example, the sensor is located outside of a body and the sample to be sensed comprises a volume of buffer that has been pumped into and out of a subcutaneous space via a tube that is made of a semi-permeable, microdialysis membrane. During the pumping process, the buffer fluid and the interstitial equilibrate in terms of glucose concentration, such that the buffer fluid exiting the body is representative of the body's systemic glucose concentration. A useful reading of glucose concentration is then obtained from the exiting buffer fluid via the sensor.

It is contemplated that a catalytic enhancement of a microdialysis membrane will enhance or improve the performance of the membrane within a subcutaneous space, in much the same way the catalytic enhancement of polymeric membranes enhanced those membranes. That is, it is contemplated that a catalyst-enhanced microdialysis membrane will be demonstrate more accurate and less noisy data relative to a non-enhanced microdialysis membrane. A superoxide-dismutase/catalase catalyst or mimic may be used for this enhancement, in any suitable manner, such as any previously described herein. Further, as previously described with regard to a sensor-covering membrane, a superoxide-dismutase/catalase catalyst or mimic may be associated with a microdialysis membrane in various ways, such as via covalent bonds, ionic interactions, and/or adsorption.

According to other embodiments of the invention, a superoxide-dismutase/catalase catalyst or mimic is included within a sensor structure, though it need not be associated with a polymeric membrane covering a surface of the sensor. As previously described, a superoxide-dismutase/catalase catalyst or mimic may be associated with a polymeric membrane in a various ways, such as via covalent bonds, ionic interactions, and/or adsorption. In some cases, the catalyst or mimic may diffuse away from the polymer; in some cases, the catalyst or mimic may remain closely bound to the polymer; and in some cases, some portion of the catalyst or mimic may remain bound to the polymer while another portion may diffuse away from the polymer. In any case, the effect of the catalyst or mimic is the lowering of the concentration of one or more metabolite(s), such as superoxide and hydrogen peroxide, in the local region of the sensing surface. This effect may be beneficial to sensor performance, as previously described and demonstrated herein.

According to the invention, a membrane may be applied to a sensor or a portion of a sensor in any useful way. That is, a membrane need not be applied directly on the sensing surface and need not fully cover the sensing surface, but may be applied less immediately and less completely relative to the sensor. Any such membrane may host one or more superoxide-dismutase/catalase catalyst, either in the form of an enzyme or a non-proteinaceous mimic, or any combination thereof. Further, a surface other than a membrane surface, or a reservoir, such as any of plastic or metallic composition, may host a catalyst or a mimic or any combination of same. By way of example, a transcutaneous sensor may have a protective medium that covers its sensing surface, but at some distance therefrom rather than immediately thereon. An inner surface of such a medium may host a superoxide-dismutase/catalase catalyst or mimic or any combination of same. Thus, various embodiments of the invention include those in which a superoxide-dismutase/catalase catalyst or mimic or any combination of same is incorporated into a membrane, such as an analyte-flux-limiting membrane, immediately overlaying the surface of a sensor, as well as those in which such a catalyst or a mimic or any combination of same is in the general locale of the surface of a sensor, though at a distance therefrom and in an amount that is sufficient to enhance the performance of the sensor. A catalyst or mimic or a combination of same, however incorporated or hosted, may act to reduce a local concentration of one or more metabolite(s), such as superoxide and hydrogen peroxide. Any such reduced local concentration of metabolite may act to slow the influx of cells from the immune system that might otherwise be recruited by any such metabolite.

The foregoing description, including the examples and embodiments therein, demonstrates various advantages of the membranes of the present invention and the sensors employing such membranes. For example, according to various aspects of the present invention, the membranes may be fairly straight-forward to manufacture, may adhere well to a sensing layer of a sensor, may effectively regulate analyte flux, such as glucose flux, and may either inhibit the recruitment of neutrophils to the sensor and/or counteract various consequences of their presence. Additionally, the membranes may serve to localize anti-neutrophil agents and/or anti-neutrophil-product agents in an immediate area of interest, such as at the sensor surface, such that any deleterious effect of neutrophils and/or any product thereof, are reduced or minimized.

Various modifications, processes, as well as numerous structures to which the present invention may be applicable will be readily apparent to those of skill in the art to which the present invention is directed upon review of the specification. Various references, publications, provisional and/or non-provisional United States patent applications, and/or United States patents, have been identified herein, each of which is incorporated herein in its entirety by this reference. Various aspects and features of the present invention may have been explained or described in relation to understandings, beliefs, theories, underlying assumptions, and/or working or prophetic examples, although it will be understood that the invention is not bound to any particular understanding, belief, theory, underlying assumption, and/or working or prophetic example. Although various aspects and features of the present invention may have been described largely with respect to applications, or more specifically, medical applications, involving diabetic humans, it will be understood that such aspects and features also relate to any of a variety of applications involving non-diabetic humans and any and all other animals. Further, although various aspects and features of the present invention may have been described largely with respect to applications involving transcutaneous sensors, it will be understood that such aspects and features also relate to any of a variety of sensors that are suitable for use in connection with the body of an animal or a human, such as those suitable for implantation within the body of an animal or a human. Finally, although the various aspects and features of the present invention have been described with respect to various embodiments and specific examples herein, all of which may be made or carried out conventionally, it will be understood that the invention is entitled to protection within the full scope of the appended claims.

The invention claimed is:

1. A membrane structure for use in an analyte sensor, comprising:
    an analyte sensing membrane comprising at least one polymer and an analyte responsive enzyme; and
    a diffusion limiting membrane comprising at least one polymer; and a catalyst, wherein the catalyst comprises a superoxide-dismutase, a catalase or a mimic of superoxide-dismutase and/or catalase; and
    wherein at least a portion of the diffusion limiting membrane is disposed directly on top of the analyte sensing membrane.

2. The membrane structure of claim 1, wherein the polymer is selected from polyvinylpyridine, a derivative of polyvinylpyridine, polyvinylimidazole, a derivative of polyvinylimidazole, or any combination thereof.

3. The membrane structure of claim 1, wherein the polymer comprises at least one functional group selected from a nitrogen group, a pyridine group, a reactive group, or any combination thereof.

4. The membrane structure of claim 1, wherein the catalyst is superoxide dismutase and/or catalase.

5. The membrane structure of claim 1, wherein the catalyst comprises a mimic of superoxide dismutase and/or catalase.

6. The membrane structure of claim 1, wherein the catalyst comprises a metal selected from manganese, iron, copper, zinc, or any combination thereof.

7. The membrane structure of claim 1, wherein the catalyst comprises manganese 5,10,15,20-tetra(4-pyridyl)-21H,23H-porphine chloride (MnTPyP).

8. The membrane structure of claim 1, wherein the catalyst comprises MnTPyP quaternized at least one pyridyl site.

9. The membrane structure of claim 1, wherein the catalyst comprises MnTPyP quarternized at at least one pyridyl site by a quaternizing moiety and a pyridyl or an amino functional group attached to at least one quaternizing moiety.

10. The membrane structure of claim 1, wherein the catalyst comprises manganese coordinated in a macrocyclic, penta-amine ring.

11. The membrane structure of claim 10, wherein the catalyst further comprises a reactive amino or pyridyl group.

12. The membrane structure of claim 1, wherein the catalyst comprises an agent having superoxide-dismutase activity and a reactive amino or pyridyl group.

13. The membrane structure of claim 12, wherein the agent comprises a transition metal chelate of pentaazacyclopentadecane.

14. The membrane structure of claim 12, wherein the agent comprises a transition metal chelate of salen.

15. The membrane structure of claim 1, wherein the catalyst comprises a bypyridine manganese complex.

16. The membrane structure of claim 1, wherein the catalyst comprises a cyclic salen-transition-metal complex.

17. The membrane structure of claim 1, wherein the catalyst comprises an agent selected from a manganese porphyrin complex, an iron porphyrin complex, a manganese polyamine complex, an iron polyamine complex, a manganese salen complex, an iron salen complex, or any combination thereof.

18. The membrane structure of claim 1, wherein the catalyst comprises a biporphyrin superoxide-dismutase/catalase mimic.

19. The membrane structure of claim 1, wherein the catalyst comprises manganese (III) tetrakis (4-benzoic acid) porphyrin (MnTBAP).

20. The membrane structure of claim 1, the membrane structure sufficient for transcutaneous use.

21. The membrane structure of claim 1, the membrane structure sufficient for use in an amperometric sensor.

22. The membrane structure of claim 1, the membrane structure sufficient for use in a glucose sensor.

* * * * *

UNITED STATES PATENT AND TRADEMARK OFFICE
CERTIFICATE OF CORRECTION

PATENT NO. : 7,699,964 B2
APPLICATION NO. : 10/819498
DATED : April 20, 2010
INVENTOR(S) : Benjamin J. Feldman et al.

It is certified that error appears in the above-identified patent and that said Letters Patent is hereby corrected as shown below:

Col. 36, lines 62-63
In claim 8 please insert the word --at-- after "quaternized" so that the claim recites "quaternized at at least one pyridyl site."

Signed and Sealed this
Twenty-second Day of March, 2011

David J. Kappos
*Director of the United States Patent and Trademark Office*